(12) United States Patent
Ferrer et al.

(10) Patent No.: US 6,284,509 B1
(45) Date of Patent: Sep. 4, 2001

(54) ENZYME WITH β-1,3-GLUCANASE ACTIVITY

(75) Inventors: Pau Ferrer, Barcelona (ES); Ivan Diers, Værløse (DK); Torben Halkier, Birkerød (DK); Lisbeth Hedegaard, Skodsborg (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/159,106

(22) Filed: Sep. 23, 1998

Related U.S. Application Data

(63) Continuation of application No. PCT/DK97/00160, filed on Apr. 14, 1997.

(30) Foreign Application Priority Data

Apr. 12, 1996 (DK) .................................................. 0427/96
Aug. 23, 1996 (DK) .................................................. 0885/96

(51) Int. Cl.[7] ............................... C12N 9/24; C12N 1/20; C12N 15/00
(52) U.S. Cl. ........................... 435/200; 435/183; 435/99; 435/243; 435/259; 435/267; 435/252.3; 435/320.1
(58) Field of Search .................................... 435/183, 200, 435/252.3, 320.1, 99, 243, 259, 267

(56) References Cited

FOREIGN PATENT DOCUMENTS

WO 92/03557   3/1992  (CA) .
WO 96/12013   4/1996  (DK) .
WO 87/01388   3/1987  (US) .

OTHER PUBLICATIONS

S. Shen et al. Primary sequence of the glucanase gene from O.xanthaneolytica. J. Biol. Chem., 1991, vol., 266:1508–1063, 1991.*

Gen Bank Accession No. M60826, 28, Jan. 1991.*

P. Ferrer et al. (1996) Journal of Bacteriology 178(15) :4751–4757.

J. Parrado et al. (1996) Biochemica et Biophysica Acta 1296:145–151.

Asenjo et al. (1996) Annals of the New York Academy of Sciences, vol. 782, "Recombinant DNA Biotechnology III: The Integration of Biological and Engineerings Sciences".

Ventom et al. (1991) Enzyme Microb. Technol. 13:71–75.

* cited by examiner

*Primary Examiner*—Rebecca E. Prouty
*Assistant Examiner*—Manjunath N. Rao
(74) *Attorney, Agent, or Firm*—Elias J. Lambiris; Jason I. Garbell

(57) ABSTRACT

The present invention relates to a DNA construct exhibiting β-1,3-glucanase activity, which DNA sequence comprises: a) the DNA sequence shown in SEQ ID No. 1 or SEQ ID No. 12, or b) an analogue of the DNA sequence defined in a), which i) is homologous with the DNA sequence defined in a), or ii) hybridizes with the same oligonucleotide probe as the DNA sequence defined in a), or iii) encodes a polypeptide which is homologous with the polypeptide encoded by a DNA sequence comprising the DNA sequence defined in a), or iv) encodes a polypeptide which is immunologically reactive with an antibody raised against the purified β-1,3-glucanase derived from *Oerksovia xanthineolytica* LLG109 encoded by the DNA sequence defined in a). The DNA construct may further encode a mannose binding domain. The invention also relates to a DNA construct encoding a mannose binding domain. Further the invention relates to an expression vector comprising said DNA constructs, a cell harbouring said DNA constructs or expression vectors, a method of producing the novel enzyme, a novel enzyme preparation containing said novel enzyme, the use of the enzyme for degrading or modification of β-glucan containing material.

9 Claims, 10 Drawing Sheets

```
          DS140
    tttgtggatgggcagcagtt..accgcg..acgcg..g.gag..cgg.g.gaa.gc..gg
1   ············································································· 60
    aaacacctacccgtcgtcaaggtggcgcagtgcgcggcgc..gagccgcg...g.ggacc

F  V  D  G  Q  Q  F  H  P  Y  T  R  R  E  L  G  A  N  A  W gtgttcgaccagccgttc.......a..c.caacgt.gcggtcggcgggcagtggccgggc
61  ············································································· 120
    tacaagctggttggcaagaaggagtaggagttgcagcgccagccgcccgtcaccggcccg

V  F  D  Q  P  F  F  L  I  L  N  V  A  V  G  G  Q  W  P  G taccccgacggcacgacccagctcccgcagcagatgaaggtcgattacgtccgcgtctac
121 ············································································· 180
    atggggctgccgtgctgggtcgagggcgtcgtctacttccagctaatgcaggcgcagatg
                                                               DS143
    Y  P  D  G  T  T  Q  L  P  Q  Q  M  K  V  D  Y  V  R  V  Y g
181 ·
      c
```

FIG 2

```
     acggaggaggagcgact gagagat gacct cgcacgt cacgct cct gaccgccagcacccg
  1  ............................................................ 60
     t gcct cct cct cgct gact ct ct act ggagcgt gcagt gcgaggact ggcggt cgt gggc
      R  R  R  S  Q  .  E  M  T  S  H  V  T  L  L  T  A  S  T  R  -
                                                              s
                                                              Ba
                                                              gc
                                                              I I
                                                              I I acggcgcgaccaccggcggcgcct gt gcagcgcgct cgt cgccgcgct cacggccgccgc
 61  ............................................................ 120
     t gccgcgct ggt ggccgccgcggacacgt cgcgcgagcagcggcgcgagt gccggcggcg
      R  R  D  H  R  R  R  L  C  S  A  L  V  A  A  L  T  A  A  A  - ggcagcgct cgccgt caccgt ggccgcgacgt cggccgccgccgcgcccggcgacccct
121  ............................................................ 180
     ccgt cgcgagcggcagt ggcaccggcgct gcagccggcggcggcgcgggccgct ggagga
      A  A  L  A  V  T  V  A  A  T  S  A  A  A  A  P  G  D  L  L  - gt ggt ccgacgagt t cgacggcgcggcgggct cggcgccgaacccggccgt ct ggaacca
181  ............................................................ 240
     caccaggct gct caagct gccgcgccgcccgagccgcggct t gggccggcagacct t ggt
      W  S  D  E  F  D  G  A  A  G  S  A  P  N  P  A  V  W  N  H  -
                                            s
                                            a
                                            c
                                            I cgagaccggcgcgcacgggt ggggcaacgccgagct ccagaact acacggct t cgcgcgc
241  ............................................................ 300
     gct ct ggccgcgcgt gcccaccccgt t gcggct cgaggt ct t gat gt gccggagcgcgcg
      E  T  G  A  H  G  W  G  N  A  E  L  Q  N  Y  T  A  S  R  A  - caact ccgcgct cgacggccagggcaacct cgt cat caccgcgcgt cgcgagggcgacgg
301  ............................................................ 360
     gt t gaggcgcgagct gccggt cccgt t ggagcagt agt ggcgcgcagcgct cccgct gcc
      N  S  A  L  D  G  Q  G  N  L  V  I  T  A  R  R  E  G  D  G  - gt cgt acacgt cggcccgcat gacgacccagggcaagt accagccgcagt acgggcgcat
361  ............................................................ 420
     cagcat gt gcagccgggcgt act gct gggt cccgt t cat ggt cggcgt cat gcccgcgt a
      S  Y  T  S  A  R  M  T  T  Q  G  K  Y  Q  P  Q  Y  G  R  I  -
```

FIG 6A

```
      cgaggcgcgcat ccagat cccgcgcggccaggggat ct ggccggcgt t ct ggat gct cgg
421   ·················································· 480
      gct ccgcgcgt aggt ct agggcgcgccggt cccct agaccggccgcaagacct acgagcc
       E  A  R  I  Q  I  P  R  G  Q  G  I  W  P  A  F  W  M  L  G   -
                AXS
                vmm
                aaa
                I I I
                  / cgggagct t ccccgggacgccgt ggccgt cgggcgagat cgacat cat ggagaacgt cgg
481   ·················································· 540
      gccct cgaaggggccct gcggcaccggcagcccgct ct agct gt agt acct ct t gcagcc
       G  S  F  P  G  T  P  W  P  S  G  E  I  D  I  M  E  N  V  G
                                         AXS
                                         vmm
                                         aaa
                                         I I I
                                           / gt t cgagccgcaccgcgt gcacggcacggt gcacggcccggggt act ccggcggct ccgg
541   ·················································· 540
      caagct cggcgt ggcgcacgt gccgt gccacgt gccgggcccat gaggccgccgaggcc
       F  E  P  H  R  V  H  G  T  V  H  G  P  G  Y  S  G  G  S  G cat cacgggcat gt accagcacccgcagggct ggt cgt t cgcggacacgt t ccacacgt t
601   ·················································· 660
      gt agt gcccgt acat ggt cgt gggcgt cccgaccagcaagcgcct gt gcaaggt gt caa
       I  T  G  M  Y  Q  H  P  Q  G  W  S  F  A  D  T  F  H  T  F  -
             H                             H
             i                             i
           S n                           S n
           a c                           a c
           I I                           I I
           I I                           I I cgcggt cgact ggaagccgggcgagat cacct ggt t cgt cgacggccagcagt t ccaccg
661   ·················································· 60
      gcgccagct gacct t cggcccgct ct agt ggaccaagcagct gccggt cgt caaggt ggc
       A  V  D  W  K  P  G  E  I  T  W  F  V  D  G  Q  Q  F  H  R   - cgt cacgcgcgagcgt cggcgcgaacgcct gggt gt t cgaccagccgt t ct t cct cat
721   ·················································· 780
      gcagt gcgcgct cgcagccgcgct t gcggacccacaagct ggt cggcaagaaggagt a
       V  T  R  A  S  V  G  A  N  A  W  V  F  D  Q  P  F  F  L  I   -
```

FIG 6B

```
         cct caacgt cgcggt cggcgggcagt ggccgggct accccgacggcacgacccagct ccc
781      ····················································· 840
         ggagt t gcagcgccagccgcccgt caccggcccgat ggggct gccgt gct gggt cgaggg
          L  N  V  A  V  G  G  Q  W  P  G  Y  P  D  G  T  T  Q  L  P  -
                   H
                   i
                   S  n                              A              AXS
                   a  c                              v              vmm
                   l  l                              a              aaa
                   l  l                              l              lll
                                                                     / gcagcagat gaaggt cgact acgt gcgcgt ct acgacaacggct cgggct cgt t gagccc
841      ····················································· 900
         cgt cgt ct act t ccagct gat gcacgcgcagat gct gt t gccgagcccgagcagct cggg
          Q  Q  M  K  V  D  Y  V  R  V  Y  D  N  G  S  G  S  S  S  P  - ggggaaccccggcaccggcct gccgacggggaccggcgcggt gcgcgccgcgt aacggca
901      ····················································· 960
         ccccttggggccgt ggccggacggct gcccct ggccgcgccacgcgcggcgcat t gccgt
          G  N  P  G  T  G  L  P  T  G  T  G  A  V  R  A  A  -  R  H  -
                   H
                   i
                   S  n
                   a  c
                   l  l
                   l  l t gt gcgt cgacgt cccgt gggcggacccgaccgacggcaacccggt gcagat cgt cacgt
961      ····················································· 1020
         acacgcagct gcagggcacccgcct gggct ggct gccgt t gggccacgt ct agcagt gca
          V  R  R  R  P  V  G  G  P  D  R  R  Q  P  G  A  D  R  H  V  - gcagcggcaacgcgccagacct ggacgcgt ggct ccgacgggaccgt ccgcgcgct cggc
1021     ···················································· 1080
         cgt cgccgt t gcgggt ct ggacct gcgcaccgaggct gccct ggcaggcgcgcgagccg
          Q  R  Q  R  A  R  P  G  R  V  A  P  T  G  P  S  A  R  S  A  - aagt gcct cgacgt gcgcgacggct cgacgacgcgcggt gcggccgt gcaggt gt ggacg
1081     ···················································· 1140
         t t cacggagct gcacgcgct gccgagct gct gcgcgccacgccggcacgt ccacacct gc
          S  A  S  T  C  A  T  A  R  R  R  A  V  R  P  C  R  C  G  R  - t gcaacgggacgggcgcgcagaagt gggcgt acgacg
1141     ·················· 1177
         acgt t gccct gcccgcgcgt ct t caccgcat gct gc
          A  T  G  R  A  R  R  S  G  R  T  T  -
```

FIG 6C

SEQUENCE LISTING

<160> NUMBER OF SEQ ID NOS: 15

<210> SEQ ID NO 1
<211> LENGTH: 1177
<212> TYPE: DNA
<213> ORGANISM: Oerskovia xanthineolytica

<400> SEQUENCE: 1

```
acggaggagg agcgactgag agatgacctc gcacgtcacg ctcctgaccg ccagcacccg      60
acggcgcgac caccggcggc gcctgtgcag cgcgctcgtc gccgcgctca cggccgccgc     120
ggcagcgctc gccgtcaccg tggccgcgac gtcggccgcc gccgcgcccg gcgacctcct     180
gtggtccgac gagttcgacg gcgcggcggg ctcggcgccg aacccggccg tctggaacca     240
cgagaccggc gcgcacgggt ggggcaacgc cgagctccag aactacacgg cctcgcgcgc     300
caactccgcg ctcgacggcc agggcaacct cgtcatcacc gcgcgtcgcg agggcgacgg     360
gtcgtacacg tcggcccgca tgacgaccca gggcaagtac cagccgcagt acgggcgcat     420
cgaggcgcgc atccagatcc cgcgcggcca ggggatctgg ccggcgttct ggatgctcgg     480
cgggagcttc cccgggacgc cgtggccgtc gggcgagatc gacatcatgg agaacgtcgg     540
gttcgagccg caccgcgtgc acggcacggt gcacggcccg gggtactccg gcggctccgg     600
catcacgggc atgtaccagc acccgcaggg ctggtcgttc gcggacacgt tccacacgtt     660
cgcggtcgac tggaagccgg gcgagatcac ctggttcgtc gacggccagc agttccaccg     720
cgtcacgcgc gcgagcgtcg gcgcgaacgc ctgggtgttc gaccagccgt tcttcctcat     780
cctcaacgtc gcggtcggcg ggcagtggcc gggctacccc gacggcacga cccagctccc     840
gcagcagatg aaggtcgact acgtgcgcgt ctacgacaac ggctcgggct cgtcgagccc     900
ggggaacccc ggcaccggcc tgccgacggg gaccggcgcg gtgcgcgccg cgtaacggca     960
tgtgcgtcga cgtcccgtgg gcggacccga ccgacgcaa cccggtgcag atcgtcacgt    1020
gcagcggcaa cgcgccagac ctggacgcgt ggctccgacg ggaccgtccg cgcgctcggc    1080
aagtgcctcg acgtgcgcga cggctcgacg acgcgcggtg cggccgtgca ggtgtggacg    1140
tgcaacggga cgggcgcgca gaagtgggcg tacgacg                            1177
```

<210> SEQ ID NO 2
<211> LENGTH: 263
<212> TYPE: PRT
<213> ORGANISM: Oerskovia xanthineolytica

<400> SEQUENCE: 2

```
Ala Pro Gly Asp Leu Leu Trp Ser Asp Glu Phe Asp Gly Ala Ala Gly
 1               5                  10                  15
Ser Ala Pro Asn Pro Ala Val Trp Asn His Glu Thr Gly Ala His Gly
             20                  25                  30
Trp Gly Asn Ala Glu Leu Gln Asn Tyr Thr Ala Ser Arg Ala Asn Ser
         35                  40                  45
Ala Leu Asp Gly Gln Gly Asn Leu Val Ile Thr Ala Arg Arg Glu Gly
     50                  55                  60
Asp Gly Ser Tyr Thr Ser Ala Arg Met Thr Thr Gln Gly Lys Tyr Gln
 65                  70                  75                  80
Pro Gln Tyr Gly Arg Ile Glu Ala Arg Ile Gln Ile Pro Arg Gly Gln
                 85                  90                  95
Gly Ile Trp Pro Ala Phe Trp Met Leu Gly Gly Ser Pro Gly Thr
            100                 105                 110
Pro Trp Pro Ser Gly Glu Ile Asp Ile Met Glu Asn Val Gly Phe Glu
        115                 120                 125
Pro His Arg Val His Gly Thr Val His Gly Pro Gly Tyr Ser Gly Gly
    130                 135                 140
Ser Gly Ile Thr Gly Met Tyr Gln His Pro Gln Gly Trp Ser Phe Ala
145                 150                 155                 160
```

Asp Thr Phe His Thr Phe Ala Val Asp Trp Lys Pro Gly Glu Ile Thr
            165                 170                 175

Trp Phe Val Asp Gly Gln Gln Phe His Arg Val Thr Arg Ala Ser Val
        180                 185                 190

Gly Ala Asn Ala Trp Val Phe Asp Gln Pro Phe Phe Leu Ile Leu Asn
            195                 200                 205

Val Ala Val Gly Gly Gln Trp Pro Gly Tyr Pro Asp Gly Thr Thr Gln
        210                 215                 220

Leu Pro Gln Gln Met Lys Val Asp Tyr Val Arg Val Tyr Asp Asn Gly
225                 230                 235                 240

Ser Gly Ser Ser Ser Pro Gly Asn Pro Gly Thr Gly Leu Pro Thr Gly
            245                 250                 255

Thr Gly Ala Val Arg Ala Ala
            260

<210> SEQ ID NO 3
<211> LENGTH: 18
<212> TYPE: DNA
<213> ORGANISM: Artificial Sequence
<220> FEATURE:
<223> OTHER INFORMATION: Primer 140D

<400> SEQUENCE: 3
gtggatgggc agcagttc                                              18

<210> SEQ ID NO 4
<211> LENGTH: 18
<212> TYPE: DNA
<213> ORGANISM: Artificial Sequence
<220> FEATURE:
<223> OTHER INFORMATION: Primer 143U

<400> SEQUENCE: 4
gtagacgcgg acgtaatc                                              18

<210> SEQ ID NO 5
<211> LENGTH: 22
<212> TYPE: DNA
<213> ORGANISM: Artificial Sequence
<220> FEATURE:
<223> OTHER INFORMATION: Primer DK1

<400> SEQUENCE: 5
gcaatcgatt gcattacgaa ag                                         22

<210> SEQ ID NO 6
<211> LENGTH: 37
<212> TYPE: DNA
<213> ORGANISM: Artificial Sequence
<220> FEATURE:
<223> OTHER INFORMATION: Primer DK2

<400> SEQUENCE: 6
gaggtcgccg ggcgcggctt cagcggcgtt tggattg                         37

<210> SEQ ID NO 7
<211> LENGTH: 36
<212> TYPE: DNA
<213> ORGANISM: Artificial Sequence
<220> FEATURE:
<223> OTHER INFORMATION: Primer DK3

<400> SEQUENCE: 7

```
aacgccgctg aagccgcgcc cggcgacctc ctgtgg              36
```

<210> SEQ ID NO 8
<211> LENGTH: 35
<212> TYPE: DNA
<213> ORGANISM: Artificial Sequence
<220> FEATURE:
<223> OTHER INFORMATION: Primer DK4

<400> SEQUENCE: 8

```
gtcggatcct gcagctgcac gtgacgatct gcacc              35
```

<210> SEQ ID NO 9
<211> LENGTH: 30
<212> TYPE: DNA
<213> ORGANISM: Artificial Sequence
<220> FEATURE:
<223> OTHER INFORMATION: Primer DK5

<400> SEQUENCE: 9

```
aacacgatcg gtcgacccgc ccgacgacgc                    30
```

<210> SEQ ID NO 10
<211> LENGTH: 1516
<212> TYPE: DNA
<213> ORGANISM: Oerskovia xanthineolytica

<400> SEQUENCE: 10

```
cggtgcagag tcgcgccgag agcatgtccc gcaccgtggc gagacgcagg cggcaccgcc    60
gccggacctg gaggaacgat ggacctcgca cgtcaccgct ccctgacccc gccccgcacc   120
ccgaccgggc gccgaccacg cgcccggcgg cgcctcgcga gcgcgctcgt cgccgcgctc   180
acggccgccg cggcagcgct cgccgtcacc gtggccgcga cgtcggccgc cgccgcgccc   240
ggcgacctcc tgtggtccga cgagttcgac ggcgcggcgg gctcggcgcc gaacccggcc   300
gtctggaacc acgagaccgg cgcgcacggg tggggcaacg ccgagctcca gaactacacg   360
gcctcgcgcg ccaactccgc gctcgacggc cagggcaacc tcgtcatcac cgcgcgtcgc   420
gagggcgacg ggtcgtacac gtcggcccgc atgacgaccc agggcaagta ccagccgcag   480
tacgggcgca tcgaggcgcg catccagatc ccgcgcggcc aggggatctg gccggcgttc   540
tggatgctcg gcgggagctt ccccgggacg ccgtggccgt cgtcgggcga gatcgacatc   600
atggagaacg tcgggttcga gccgcaccgc gtgcacggca cggtgcacgg cccggggtac   660
tccggcgggct ccggcatcac gggcatgtac cagcacccgc agggctggtc gttcgcggac   720
acgttccaca cgttcgcggt cgactggaag ccgggcgaga tcacctggtt cgtcgacggc   780
cagcagttcc accgcgtcac gcgcgcgagc gtcggcgcga acgcctgggt gttcgaccag   840
ccgttcttcc tcatcctcaa cgtcgcggtc ggcgggcagt ggccgggcta ccccgacggc   900
acgacccagc tcccgcagca gatgaaggtc gactacgtgc gcgtctacga caacggctcg   960
ggctcgtcga gccggggaa ccccggcacc ggcctgccga cggggaccgg cgcggtgcgc  1020
gccgcgaacg gcatgtgcgt cgacgtcccg tgggcggacc cgaccgacgg caacccggtg  1080
cagatcgtca cgtgcagcgg caacgccgcc cagacctgga cgcgtggctc cgacgggacc  1140
gtccgcgcgc tcggcaagtg cctcgacgtg cgcgacggct cgacgacgcg cggtgcggcc  1200
gtgcaggtgt ggacgtgcaa cgggacgggc gcgcagaagt gggcgtacga cgcggggagc  1260
aaggcgctgc gcaacccgca gtccgggctc tgcctcgacg ccacgggcgg cgcgcccctg  1320
```

```
cgcgacggcc agcggctgca gacctggacg tgcaacggca cgaccgccca gcagtggacg   1380
ctctgacacc cggctgacct ggctccgcgg cgaccggccg cgcgggcggg gcaccccggg   1440
gtgcgtcacc cgcgcgcggt cgccgcgtcg tcgggcgggt cgacgcgcgg gcccggctcg   1500
ccctgctcgc ccggtc                                                   1516
```

<210> SEQ ID NO 11
<211> LENGTH: 435
<212> TYPE: PRT
<213> ORGANISM: Oerskovia xanthineolytica

<400> SEQUENCE: 11

```
Met Asp Leu Ala Arg His Arg Ser Leu Thr Pro Pro Arg Thr Pro Thr
  1               5                  10                  15

Gly Arg Arg Pro Arg Ala Arg Arg Leu Ala Ser Ala Leu Val Ala
                 20                  25                  30

Ala Leu Thr Ala Ala Ala Ala Leu Ala Val Thr Val Ala Ala Thr
             35                  40                  45

Ser Ala Ala Ala Pro Gly Asp Leu Leu Trp Ser Asp Glu Phe Asp
         50                  55                  60

Gly Ala Ala Gly Ser Ala Pro Asn Pro Ala Val Trp Asn His Glu Thr
 65                  70                  75                  80

Gly Ala His Gly Trp Gly Asn Ala Glu Leu Gln Asn Tyr Thr Ala Ser
                 85                  90                  95

Arg Ala Asn Ser Ala Leu Asp Gly Gln Gly Asn Leu Val Ile Thr Ala
                100                 105                 110

Arg Arg Glu Gly Asp Gly Ser Tyr Thr Ser Ala Arg Met Thr Thr Gln
            115                 120                 125

Gly Lys Tyr Gln Pro Gln Tyr Gly Arg Ile Glu Ala Arg Ile Gln Ile
        130                 135                 140

Pro Arg Gly Gln Gly Ile Trp Pro Ala Phe Trp Met Leu Gly Gly Ser
145                 150                 155                 160

Phe Pro Gly Thr Pro Trp Pro Ser Ser Gly Glu Ile Asp Ile Met Glu
                165                 170                 175

Asn Val Gly Phe Glu Pro His Arg Val His Gly Thr Val His Gly Pro
            180                 185                 190

Gly Tyr Ser Gly Gly Ser Gly Ile Thr Gly Met Tyr Gln His Pro Gln
        195                 200                 205

Gly Trp Ser Phe Ala Asp Thr Phe His Thr Phe Ala Val Asp Trp Lys
    210                 215                 220

Pro Gly Glu Ile Thr Trp Phe Val Asp Gly Gln Gln Phe His Arg Val
225                 230                 235                 240

Thr Arg Ala Ser Val Gly Ala Asn Ala Trp Val Phe Asp Gln Pro Phe
                245                 250                 255

Phe Leu Ile Leu Asn Val Ala Val Gly Gly Gln Trp Pro Gly Tyr Pro
            260                 265                 270

Asp Gly Thr Thr Gln Leu Pro Gln Gln Met Lys Val Asp Tyr Val Arg
        275                 280                 285

Val Tyr Asp Asn Gly Ser Gly Ser Ser Pro Gly Asn Pro Gly Thr
    290                 295                 300

Gly Leu Pro Thr Gly Thr Gly Ala Val Arg Ala Ala Asn Gly Met Cys
305                 310                 315                 320

Val Asp Val Pro Trp Ala Asp Pro Thr Asp Gly Asn Pro Val Gln Ile
                325                 330                 335
```

```
Val Thr Cys Ser Gly Asn Ala Ala Gln Thr Trp Thr Arg Gly Ser Asp
            340                 345                 350

Gly Thr Val Arg Ala Leu Gly Lys Cys Leu Asp Val Arg Asp Gly Ser
            355                 360                 365

Thr Thr Arg Gly Ala Ala Val Gln Val Trp Thr Cys Asn Gly Thr Gly
        370                 375                 380

Ala Gln Lys Trp Ala Tyr Asp Ala Gly Ser Lys Ala Leu Arg Asn Pro
385                 390                 395                 400

Gln Ser Gly Leu Cys Leu Asp Ala Thr Gly Gly Ala Pro Leu Arg Asp
                405                 410                 415

Gly Gln Arg Leu Gln Thr Trp Thr Cys Asn Gly Thr Thr Ala Gln Gln
                420                 425                 430

Trp Thr Leu
        435

<210> SEQ ID NO 12
<211> LENGTH: 987
<212> TYPE: DNA
<213> ORGANISM: Oerskovia xanthineolytica

<400> SEQUENCE: 12
cggtgcagag tcgcgccgag agcatgtccc gcaccgtggc gagacgcagg cggcaccgcc      60
gccggacctg gaggaacgat ggacctcgca cgtcaccgct ccctgacccc gccccgcacc     120
ccgaccgggc gccgaccacg cgcccggcgg cgcctcgcga gcgcgctcgt cgccgcgctc     180
acggccgccg cggcagcgct cgccgtcacc gtggccgcga cgtcggccgc cgccgcgccc     240
ggcgacctcc tgtggtccga cgagttcgac ggcgcggcgg gctcggcgcc gaacccggcc     300
gtctggaacc acgagaccgg cgcgcacggg tggggcaacg ccgagctcca gaactacacg     360
gcctcgcgcg ccaactccgc gctcgacggc cagggcaacc tcgtcatcac cgcgcgtcgc     420
gagggcgacg ggtcgtacac gtcggcccgc atgacgaccc agggcaagta ccagccgcag     480
tacgggcgca tcgaggcgcg catccagatc ccgcgcggcc aggggatctg gccggcgttc     540
tggatgctcg gcgggagctt ccccgggacg ccgtggccgt cgtcgggcga gatcgacatc     600
atggagaacg tcgggttcga gccgcaccgc gtgcacggca cggtgcacgg cccggggtac     660
tccggcggct ccggcatcac gggcatgtac cagcacccgc agggctggtc gttcgcggac     720
acgttccaca cgttcgcggt cgactggaag ccgggcgaga tcacctggtt cgtcgacggc     780
cagcagttcc accgcgtcac gcgcgcgagc gtcggcgcga acgcctgggt gttcgaccag     840
ccgttcttcc tcatcctcaa cgtcgcggtc ggcgggcagt ggccgggcta ccccgacggc     900
acgacccagc tcccgcagca gatgaaggtc gactacgtgc gcgtctacga caacggctcg     960
ggctcgtcga gcccggggaa ccccggc                                         987

<210> SEQ ID NO 13
<211> LENGTH: 303
<212> TYPE: PRT
<213> ORGANISM: Oerskovia xanthineolytica

<400> SEQUENCE: 13

Met Asp Leu Ala Arg His Arg Ser Leu Thr Pro Pro Arg Thr Pro Thr
  1               5                  10                  15

Gly Arg Arg Pro Arg Ala Arg Arg Leu Ala Ser Ala Leu Val Ala
             20                  25                  30

Ala Leu Thr Ala Ala Ala Ala Ala Leu Ala Val Thr Val Ala Ala Thr
         35                  40                  45
```

-continued

```
Ser Ala Ala Ala Ala Pro Gly Asp Leu Leu Trp Ser Asp Glu Phe Asp
    50                  55                  60

Gly Ala Ala Gly Ser Ala Pro Asn Pro Ala Val Trp Asn His Glu Thr
65                  70                  75                  80

Gly Ala His Gly Trp Gly Asn Ala Glu Leu Gln Asn Tyr Thr Ala Ser
                85                  90                  95

Arg Ala Asn Ser Ala Leu Asp Gly Gln Gly Asn Leu Val Ile Thr Ala
                100                 105                 110

Arg Arg Glu Gly Asp Gly Ser Tyr Thr Ser Ala Arg Met Thr Thr Gln
        115                 120                 125

Gly Lys Tyr Gln Pro Gln Tyr Gly Arg Ile Glu Ala Arg Ile Gln Ile
    130                 135                 140

Pro Arg Gly Gln Gly Ile Trp Pro Ala Phe Trp Met Leu Gly Gly Ser
145                 150                 155                 160

Phe Pro Gly Thr Pro Trp Pro Ser Ser Gly Ile Asp Ile Met Glu
                165                 170                 175

Asn Val Gly Phe Glu Pro His Arg Val His Gly Thr Val His Gly Pro
                180                 185                 190

Gly Tyr Ser Gly Gly Ser Gly Ile Thr Gly Met Tyr Gln His Pro Gln
                195                 200                 205

Gly Trp Ser Phe Ala Asp Thr Phe His Thr Phe Ala Val Asp Trp Lys
    210                 215                 220

Pro Gly Glu Ile Thr Trp Phe Val Asp Gly Gln Gln Phe His Arg Val
225                 230                 235                 240

Thr Arg Ala Ser Val Gly Ala Asn Ala Trp Val Phe Asp Gln Pro Phe
                245                 250                 255

Phe Leu Ile Leu Asn Val Ala Val Gly Gly Gln Trp Pro Gly Tyr Pro
                260                 265                 270

Asp Gly Thr Thr Gln Leu Pro Gln Gln Met Lys Val Asp Tyr Val Arg
        275                 280                 285

Val Tyr Asp Asn Gly Ser Gly Ser Ser Ser Pro Gly Asn Pro Gly
    290                 295                 300
```

<210> SEQ ID NO 14
<211> LENGTH: 529
<212> TYPE: DNA
<213> ORGANISM: Oerskovia xanthineolytica

<400> SEQUENCE: 14

```
accggcctgc cgacgggac cggcgcggtg cgcgccgcga acggcatgtg cgtcgacgtc      60
ccgtgggcgg acccgaccga cggcaacccg gtgcagatcg tcacgtgcag cggcaacgcc     120
gcccagacct ggacgcgtgg ctccgacggg accgtccgcg cgctcggcaa gtgcctcgac    180
gtgcgcgacg gctcgacgac gcgcggtgcg gccgtgcagg tgtggacgtg caacgggacg    240
ggcgcgcaga agtgggcgta cgacgcgggg agcaaggcgc tgcgcaaccc gcagtccggg    300
ctctgcctcg acgccacggg cggcgcgccc ctgcgcgacg ccagcggct gcagacctgg    360
acgtgcaacg gcacgaccgc ccagcagtgg acgctctgac accggctga cctggctccg    420
cggcgaccgg ccgcgcgggc ggggcacccc ggggtgcgtc acccgcgcgc ggtcgccgcg    480
tcgtcgggcg gtcgacgcg cgggcccggc tcgccctgct cgcccggtc                 529
```

<210> SEQ ID NO 15
<211> LENGTH: 132
<212> TYPE: PRT

```
-continued

<213> ORGANISM: Oerskovia xanthineolytica

<400> SEQUENCE: 15

Thr Gly Leu Pro Thr Gly Thr Gly Ala Val Arg Ala Ala Asn Gly Met
1               5                   10                  15

Cys Val Asp Val Pro Trp Ala Asp Pro Thr Asp Gly Asn Pro Val Gln
            20                  25                  30

Ile Val Thr Cys Ser Gly Asn Ala Ala Gln Thr Trp Thr Arg Gly Ser
        35                  40                  45

Asp Gly Thr Val Arg Ala Leu Gly Lys Cys Leu Asp Val Arg Asp Gly
    50                  55                  60

Ser Thr Thr Arg Gly Ala Ala Val Gln Val Trp Thr Cys Asn Gly Thr
65                  70                  75                  80

Gly Ala Gln Lys Trp Ala Tyr Asp Ala Gly Ser Lys Ala Leu Arg Asn
                85                  90                  95

Pro Gln Ser Gly Leu Cys Leu Asp Ala Thr Gly Gly Ala Pro Leu Arg
            100                 105                 110

Asp Gly Gln Arg Leu Gln Thr Trp Thr Cys Asn Gly Thr Thr Ala Gln
        115                 120                 125

Gln Trp Thr Leu
        130
```

ENZYME WITH β-1,3-GLUCANASE ACTIVITY

CROSS-REFERENCE TO RELATED APPLICATIONS

This application is a continuation of PCT/DK97/00160 filed Apr. 14, 1997 and claims priority under 35 U.S.C. 119 of Danish applications 0427/96 filed Apr. 12, 1996, and 0885/96 filed Aug. 23, 1996, the contents of which are fully incorporated herein by reference.

FIELD OF THE INVENTION

The present invention relates to an enzyme exhibiting β-1,3-glucanase activity derivable from *Oerskovia xanthineolytica*. More specifically a DNA construct encoding said enzyme, an expression vector comprising said DNA construct or said recombinant expression vector, a method of producing said novel enzyme, an enzyme preparation comprising said novel enzyme, and use of the enzyme for degradation or modification of β-glucan containing material.

BACKGROUND OF THE INVENTION

A large diverse group of nonmotile, heterotrophic, eukaryotic organisms is collectively referred to as fungi. Most fungi are saprophytes, i.e. securing their food from dead organic material. Due to their heterotrophic properties, i.e. using organic material as carbon source, many fungi produce metabolites of industrial interest. Certain species are further useful as sources for food, whereas others are responsible for spoiling almost any organic material with which they come in contact.

Fungal cells range in size from microscopic unicellular organism to macroscopic as e.g. mushrooms. True fungi are in general terrestrial and includes *Zygomycetes*, such as *Rhizopus, Basidiomycetes* such as *Puccinia graminis. Ascomycetes*, such as *Neurospora* and *Saccharomyces* and *Deuteromycetes*, such as *Pencillium* and *Aspergillus*.

Fungal cells

Fungal microorganisms include multicellular as well as unicellular organisms, and are in general considered to consist of yeast and molds. Unicellular fungi are primarily named yeast, while the term mold is used for fungi that are predominantly mycelial.

Fungal cells have a quite complex structure, constituted by a cytoplasm, comprising nucleus, mitochondria, microbodies etc. encapsulated by a cytoplasmic membrane. Chemically and structurally the cytoplasmic membrane consists of a bilayer of phospholipids with different proteins inserted.

The cytoplasmic membrane is surrounded by the rigid cell wall.

Structure of fungal cell walls

The cell walls of most true fungal microorganisms contain a network of glucan, which gives the cell wall strength. Further major fungal cell walls constituents are mannoprotein and chitin.

Glucan and chitin are far more resistant to microbial degradation than cellulose, which is the major constituent of the cell wall of many fungi-like organisms, such as *Oomycetes*.

Glucan is predominantly β-1,3-linked with some branching via 1,6-linkage (Manners et al., Biotechnol. Bioeng, 38, p. 977, 1973), and is known to be degradable by certain β-1,3-glucanase systems.

β-1,3-glucanase includes the group of endo-β-1,3-glucanases also called laminarinases (E.C. 3.2.1.39 and E.C. 3.2.1.6, Enzyme Nomenclature, Academic Press, Inc. 1992).

Pegg et al., Physiol. Plant Pethol., 21, p. 389–409, 1982, showed that a purified endo-β-1,3-glucanase from tomato in combination with an exo-β-1,3-glucanase of fungal origin were capable of hydrolysing isolated cell wall of the fungus *Verticillium alboatrum*.

Further, Keen et al., Plant Physiol., 71, p. 460–465 showed that a purified β-1,3-glucanase from soy bean was capable of degrading isolated cell walls of fungi.

Large scale degradation of the fungal cell wall

The unit operation of cell disrupture appears as an essential first step for intracellular products separation and downstream processing of valuable intracellular products.

Large scale cell disrupture is in general carried out by rather vigorous treatment involving the use of strong chemicals and/or mechanical means. This leaves the target protein with a very complex mixture of contaminants.

In this context, extensive industrial implementation of alternative approaches to conventional microbial cell disrupture technique is becoming of increasing relevance (Asenjo et al., Bio/technol 11, p. 214, 1993; De la Fuente et al., (1993), Appl. Microbiol. Biotechnol 38, p. 763).

Selective Cell Permeabilization (SCP) and Selective Protein Recovery (SPR) as a means for increasing bioprocess productivity, economy and product quality by simplifying the downstream processing of intracellular products have proved to be very attractive in terms of their delicacy and specificity (Asenjo et al., (1993), supra; Shen et al., Gene 84, p. 1989).

SCP and SPR involve the use of pure preparations of cell-wall-degrading β-glucanases to increase fungal cell wall porosity (with very limited cell lysis) and facilitate the release of intracellular proteins. In this way, SCP gives primary separation of the target product from some of its major contaminants. A major limitation to this approach is the relatively low level of expression of yeast lytic enzymes presently obtained in the bacteria used for the production of these enzymes (e.g. *Oerskovia xanthineolytica*, Andrews and Asenjo, (1987), Biotech. Bioeng 30, p. 628).

A number of commercial enzyme compositions useful in the enzymatic lysis of fungal cells are available. Such products normally comprise multiple enzymatic activities, e.g. including β-1,3- and β-1,6-glucanase, protease, chitinase, mannase and other enzymes capable of degrading cell wall components.

The lytic system of *Oerskovia xanthineolytica* LLG109

The lytic enzyme system of *Oerskovia xanthineolytica*LLG109 has partially been isolated and purified and some of the glucanase and protease components have been characterised (Ventom and Asenjo, (1991), Enzyme Microb. Technol. 13, p. 71).

Although a single molecular species of lytic β-1,3-glucanase has been characterized from *O. xanthineolytica* LLG109, most *Oerskovia* strains seem to have multiple β-1,3-glucanase systems (Doi and Doi, (1986), J. Bacteriol. 168, 1272).

While all observed molecular forms of these enzymes possess hydrolytic activity towards β-1,3-glucans (β-1,3-glucanase activity) only some are found capable of readily solubilizing yeast glucan and inducing lysis of viable yeast cells.

In contrast, other types of endo-β-1,3-glucanases would solubilize yeast glucan only partially, causing only limited cell lysis (Doe and Doi. (1986), supra). However, this multitude of enzyme species produced by *Oerksovia* may be partially due to proteolytic processing.

The genetic relationship between these enzymes is still unclear, as the number of yeast lytic enzymes so far cloned is very limited. As a result, limited knowledge still exists about the gene structure and protein function relationship (Shen et al, (1991), J. Biol. Chem. 266, p. 1058; Shimol and Tademura, (1991), J. Biochem. 110, p. 608; Watanabe et al., (1992), J. Bacteriol. 174(1), p. 186; Yamamoto et al., (1993), Biosci. Biotechnol. Biochem. 57, p. 1518–1525).

Characterization of yeast lytic enzymes from *O. xanthineolytica*

A Purified lytic β-1,3-glucanase showed a molecular mass of about 31 kDa, when estimated by SDS-PAGE and a pI of 5.0. The amino acid composition was also determined. The yield was optimized by the continuous culture process, but yields were still low.

The specific activity of the enzyme was 11.1 U/mg. The $K_n$ for β-1,3-glucanase activity on yeast glucan was 2.5 mg/ml, for laminarin (a soluble β-1,3-glucan) 0.95 mg/ml. The pH optimum for β-1,3-glucanase was 8.0 yeast glucan and 6.0 on laminarin substrate. The lytic β-1,3-glucanase caused only limited lytic activity on viable yeast (*Saccharomyces cerevisiae*) cells (Ventom and Asenjo, (1991), supra), but this was stimulated synergistically by the lytic protease component.

In addition, another β-1,3-glucanase component was detected in clarified *O. xanthineolytica* continuous fermentation broth, although it was not purified to homogeneity and subsequently characterized.

Patent documents

A number of β-1,3-glucanase genes and uses thereof have been sought patented.

An example is DD 226012 (Akad. Wissenshaft, DDR) which concerns a method for production of a *Bacillus* β-1,3-glucanase.

Further, JP 61040792 A (DOI K) describes a cell wall-cytolase β-1,3-glucanase recombinant plasmid for removing the cell walls of yeast. The gene is derived from *Arthrobacter* and is transformed in *Escherichia* group bacteria.

EP 440.304 concerns plants provided with improved resistance against pathogenic fungi transformed with at least one gene encoding an intracellular chitinase, or in intra- or extracellular β-1,3-glucanase. The matching recombinant polynucleotides is also disclosed.

WO 87/01388 (The Trustees of Columbia University) describes a method for preparing cell lytic enzymes, such as β-1,3-glucanases, which can be produced by *Oerksovia*.

WO 92/03557 (Majesty (Her) in Right of Canada) discloses a recombinant DNA expression vector comprising a 2.7 kb DNA sequence, derived from *Oerskovia xanthineolytica*, encoding a β-1,3-glucanase. Said glucanase, expressed in *E. coli*, exhibits glucanase activity, and no protease activity.

*E. coli* has a number of deficiencies in connection with large scale industrial enzyme production. First of all the glucanase is expressed intercellulary. Consequently the cells need to be opened to get access to the enzyme. This makes recovery of the enzyme cumbersome and expensive.

From WO 92/16632 a recombinant DNA sequence coding for a novel protein with β-1,3-glucanase activity, is known. The gene is derived from soy.

Comments concerning prior art

Most presently available enzyme preparations for the use of lysing fungal cells contain protease activity, which leaves the lysed target protein with a very complex mixture of contaminants.

It is therefore desirable to provide a β-1,3-glucanase substantially free of protease activity, which is capable of opening the cell walls in a gentle way. This will facilitate the recovery and purification of the target protein.

Further it would be advantageous to express the gene encoding the target protein in a heterologous host cell, capable of increasing the production yield.

SUMMARY OF THE INVENTION

The present inventors have succeeded in solving some of the above mentioned problems by providing enzyme(s) exhibiting β-1,3-glucanase.

First of all they have isolated and characterized a DNA sequence encoding a novel enzyme exhibiting β-1,3-glucanase activity, from which it is possible to prepare a novel single-component enzyme.

The inventors found that a mannose binding domain was hinged to the C-terminal of the β-1,3-glucanase encoding domain of the gene. The mannose binding domain glues to the enzyme substrate and result in lytic activity when hinged to a β-1,3-glucanase.

In the first aspect the invention relates to a DNA construct which comprises a DNA sequence, which DNA sequence comprises a) a β-1,3-glucanase activity encoding part of the DNA sequence shown in SEQ ID No. 1 or SEQ ID No. 12, or b) an analogue of the DNA sequence defined in a), which
  i) is homologous with the DNA sequence defined in a), or
  ii) hybridizes with the same oligonucleotide probe as the DNA sequence defined in a), or
  iii) encodes a polypeptide which is homologous with the polypeptide encoded by a DNA sequence comprising the DNA sequence defined in a), or
  iv) encodes a polypeptide which is immunologically reactive with an antibody raised against the purified β-1,3-glucanase derived from *Oerskovia xanthineolytica* LLG109 encoded by the DNA sequence defined in a).

The invention also relates to a DNA construct comprising a DNA sequence encoding a mannose binding domain, which DNA sequence comprises
a1) the part of the DNA sequence shown in SEQ ID No. 14 encoding a mannose binding domain,
b) an analogue of the DNA sequence defined in a1, which
  i) is homologous with the DNA sequence defined in a1), or
  ii) hybridizes with the same oligonucleotide probe as the DNA sequence defined in a1), or
  iii) encodes a polypeptide which is homologous with the polypeptide encoded by a DNA sequence comprising the DNA sequence defined in a1), or
  iv) encodes a polypeptide which is immunologically reactive with an antibody raised against the purified mannose binding domain derived from *Oerksovia xanthineolytica* LLG109 encoded by the DNA sequence defined in a1).

Furthermore, the invention also relates to a DNA construct comprising a DNA sequence encoding an enzyme exhibiting β-1,3-glucanase activity having a mannose binding domain, which DNA sequence comprises
a2) the part of the DNA sequence shown in SEQ ID No. 10 encoding a β-1,3-glucanase with a mannose binding domain.
b2) an analogue of the DNA sequence defined in a2), which
  i) is homologous with the DNA sequence defined in a2), or
  ii) hybridizes with the same oligonucleotide probe as the DNA sequence defined in a2), or
  iii) encodes a polypeptide which is homologous with the polypeptide encoded by a DNA sequence comprising the DNA sequence defined in a2), or iv) encodes a polypeptide which is immunologically reactive with an antibody raised against the purified β-1,3-glucanase with a mannose binding domain derived from *Oerskovia xanthineolytica* LLG109 encoded by the DNA sequence defines in a2).

In the present context, the expression "analogue" of the DNA sequence shown in SEQ ID No. 1, 10, 12 and 14 is intended to indicate any DNA sequence encoding polypeptides, which has the properties i)–iv) above. Typically, the analogous DNA sequence is isolated from another or related (e.g. the same) organism known or contemplated to produce an enzyme with β-1,3-glucanase activity or having a mannose binding doamin on the basis of any of the DNA sequences shown in SEQ ID No. 1, 10, 12 and 14, e.g. using the procedures described herein, or is constructed on the basis of any of the DNA sequences shown in SEQ ID No. 1, 10, 12, and 14 e.g. by introduction of nucleotide substitutions, which do not give rise to another amino acid sequence of the β-1,3-glucanase or the mannose binding doamin encoded by the DNA sequences, but which correspond to the codon usage of the host organism intended for production of the enzyme(s), or by introduction of nucleotide substitutions which do give rise to a different amino acid sequence and therefore, possibly, a different protein structure which might give rise to a mutant with different properties than the native enzymes. Other examples of possible modification are insertion of one or more nucleotides into the sequence(s), addition of one or more nucleotides at either end of the sequence (s), or deletion of one or more nucleotides at either end or within the sequence. For instance, the analogous DNA sequence(s) may be a subsequence of any of the DNA sequence(s) shown in SEQ ID No. 1, 10, 12, and 14 for which the encoded protein exhibits β-1,3-glucanase activity and/or encoding a mannose binding doamin.

The homology referred to in i) above is determined as the degree of identity between two sequences indicating a derivation of the first sequence from the second. The homology may suitably be determined by means of computer programs known in the art such as GAP provided in the GCG program package (Needleman, S. B. and Wunsch, C. D., (1970), Journal of Molecular Biology 48, p. 443–453). Using GAP with the following settings for DNA sequence comparison: GAP creation penalty of 5.0 and GAP extension penalty of 0.3, the coding region of the DNA sequence exhibits a degree of identity preferably of at least 60%, more preferably at least 70%, more preferably at least 75%, more preferably at least 80%, even more preferably at least 85%, especially at least 90%, with the coding region of the DNA sequence shown in SEQ ID No. 1, 10, 12, and 14.

The hybridization referred to in ii) above is intended to indicate that the analogous DNA sequence hybridizes to the same probe as the DNA sequence encoding the novel β-1,3-glucanase and/or the mannose binding domain under certain specified conditions, which are described in detail in the Materials and Methods section hereinafter.

Normally, analogous DNA sequence(s) is(are) highly homologous to the DNA sequence(s) such as at least 60% homologous to any of the sequences shown above encoding a β-1,3-glucanase and/or the mannose binding domain of the invention, such as at least 70%, at least 75%, at least 80%, at least 85%, at least 90% or even at least 95% homologous to any of the sequences shown above.

The degree of homology referred to in iii) above is determined as the degree of identity between two sequences indicating a derivation of the first sequence from the second. The homology may suitably be determined by means of computer programs known in the art. Typically, the polypeptide encoded by an analogous DNA sequence exhibits a degree of homology of at least 60%, such as at least 70%, 75%, 80%, 85%, 90%, 95% with the enzyme encoded by a DNA construct comprising the DNA sequence SEQ ID No. 1, 10, 12 and 14.

The term "derived from" in connection with property iv) above is intended not only to indicate a β-1,3-glucanase and/or mannose binding doamin produced by *Oerskovia xanthineolytica* LLG109, but also a β-1,3-glucanase and/or mannose binding site encoded by a DNA sequence isolated from *Oerskovia xanthineolytica* LLG109 and produced in a host organism transformed with a vector comprising said DNA sequence.

The immunological reactivity may be determined by the method described in the Materials and Methods section below.

In a further aspect, the invention relates to the construction of an expression vector harbouring a DNA construct of the invention, a cell comprising the DNA construct or expression vector, and a method of producing a novel enzyme exhibiting β-1,3-glucanase with/without a mannose binding site or the mannose bing domain itself, which method comprises culturing said cell under conditions permitting the production of the protein, and recovering the protein from the culture.

In a still further aspect, the invention relates to a novel enzyme exhibiting β-1,3-glucanase activity with/without a mannose binding domain and the mannose binding domain itself, which protein a) is encoded by a DNA construct of the invention, b) produced by the method of the invention, and/or c) is immunologically reactive with an antibody raised against a purified β-1,3-glucanase with/without a mannose binding site or the mannose binding site itself encoded by the DNA sequences shown in SEQ ID NO. 1, 10, 12 and 14 derived from *Oerskovia xanthineolytica* LLG109.

The amino acid sequence of the active enzyme with β-1,3-glucanase activity of the invention is shown in SEQ ID No. 2 (corrected in SEQ ID NO. 13). The amino acid sequence of the mannose binding domain is shown in SEQ ID no. 15, and the full length amino acid sequence is shown in SEQ ID NO. 11 (i.e. β-1,3-glucanase with a mannose binding domain).

The present invention also relates to an enzyme preparation useful for the degradation or modification of β-glucan containing materials, in particular microbial cell wall material said composition being enriched by an enzyme exhibiting β-1,3-glucanase activity with/without a mannose bind domain, as described above.

Finally contemplated according to the invention is the use of the novel enzyme or the enzyme preparation for preparation of fungal protoplasts or fungal extracts, especially yeast extracts.

The final object of the invention is to provide a process for recovery of biological components from fungal cells, by subjecting the fungal cells in question to the novel β-1,3-glucanase with/without a mannose binding domain or an enzyme preparation thereof.

stearothermophilus, sp: RBS and signal peptide-coding regions from the maltogenic α-amylase from *G. stearothermophilus*. Cat: Chloramphenicol resistance gene.

FIG. 2 shows the nucleotide sequence and the deduced amino acid sequence of the 180 bp PCR fragment cloned into the SmaI site of the pUC18vector.

Figure 3:
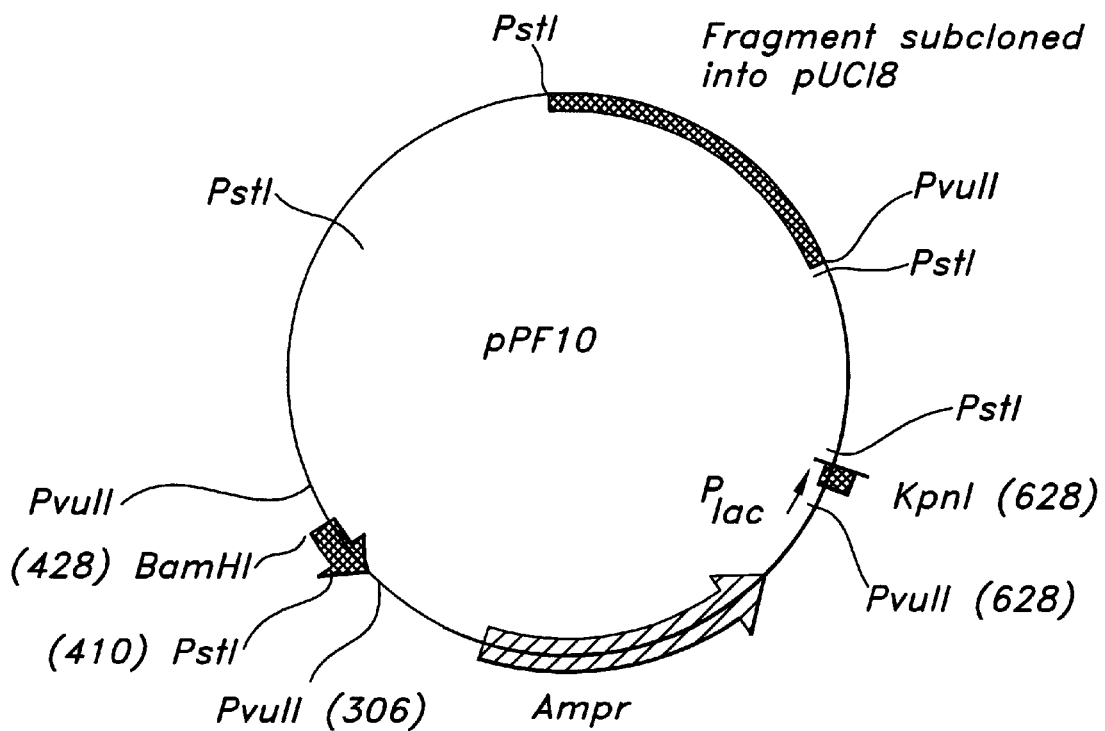

FIG. 3 shows the map of plasmid pPF10 (comprising a 7.1 kb BamHI-KpnI fragment in pUC18 and part thereof being the 2.25 kb PstI fragment and the part being the 2.0 kb PstI fragment).

Figure 4:
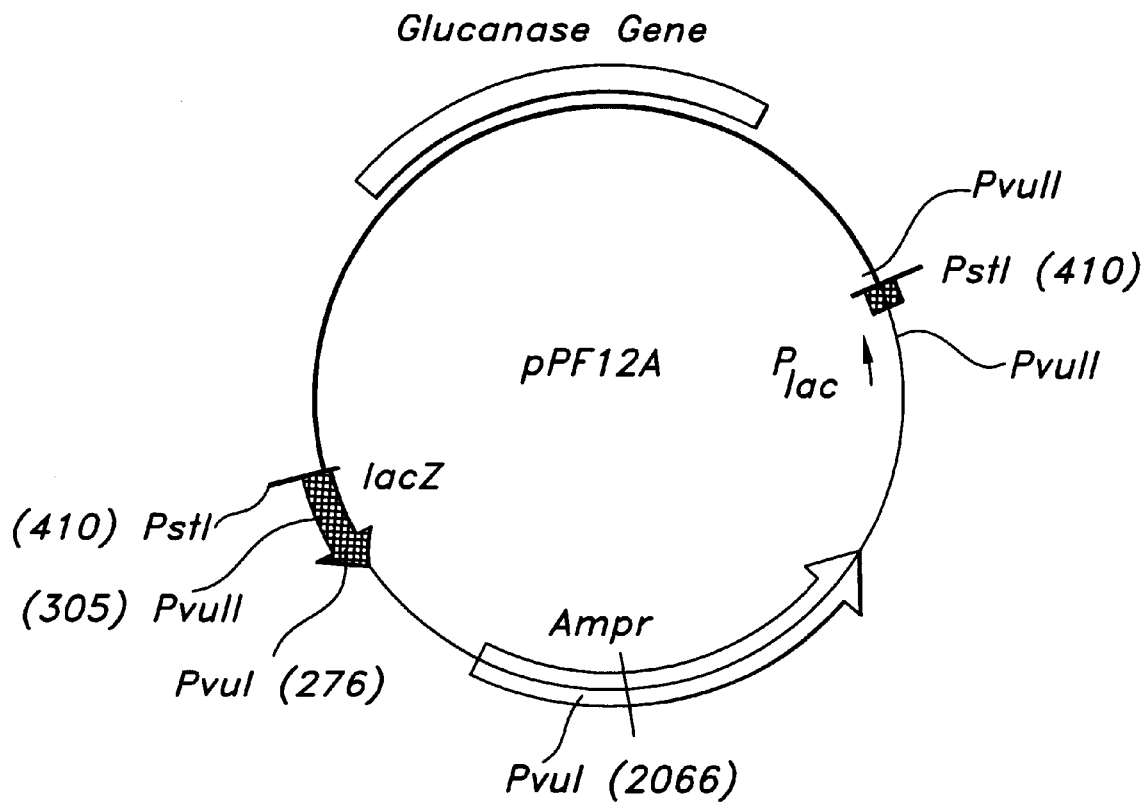

FIG. 4 shows the map of plasmid pPF12A (comprising the 2.25 kb PstI fragment).

Figure 5:
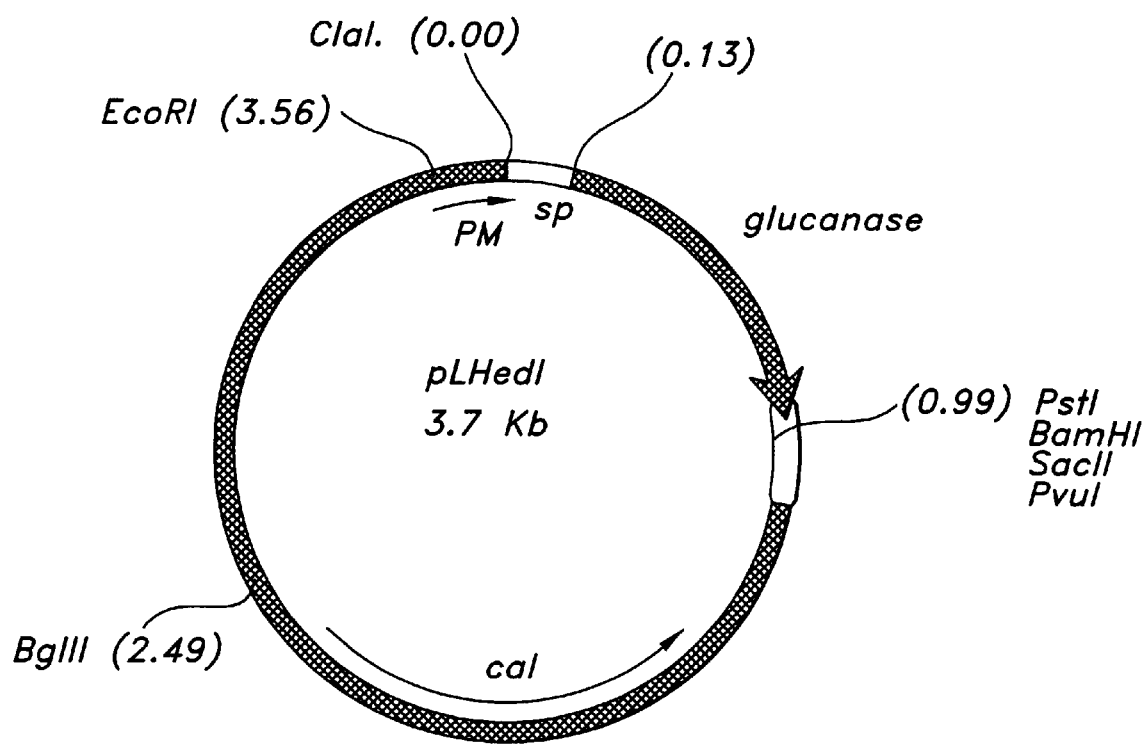

FIG. 5 shows the physical map of pLHed1. PM: Promoter from the maltogenic α-amylase from B. stearothermophilus. Sp: RBS and signal peptide-coding regions from the maltogenic α-amylase from B. stearothermophilus. Cat: Chloramphenicol resistance gene. Glucanase: The gene encoding the enzyme with β-1,3-glucanase activity of the invention.

FIG. 6 shows a part of the 2.25 kb fragment comprising the gene encoding the enzyme with β-1,3-glucanase activity of the invention and the deduced amino acid sequence with indication of restriction sites.

Figure 7:
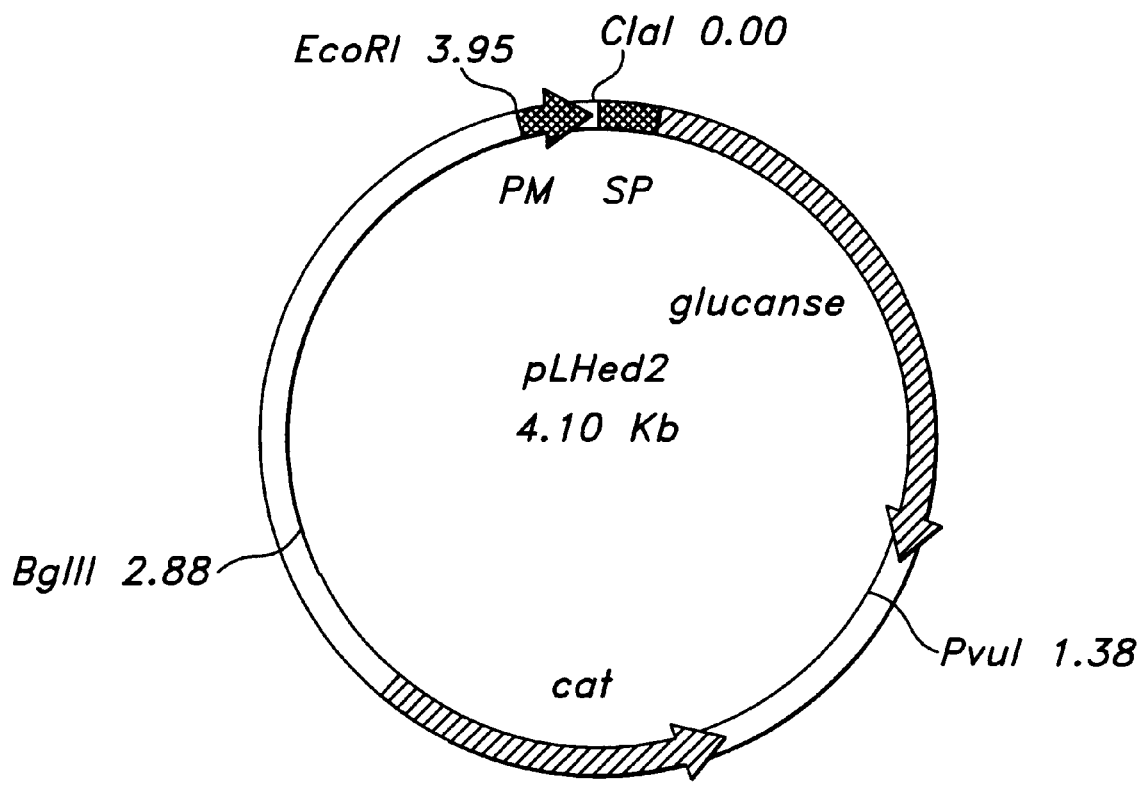

FIG. 7 shows the physical map of pLHed2. PM: Promoter from the maltogenic α-amylase from B. stearothermophilus. Sp: RBS and signal peptide-coding regions from the maltogenic α-amylase from B. stearothermophilus, Cat: Chloramphenicol resistance gene. Glucanase: The gene encoding the enzyme with β-1,3-glucanase and mannose binding site of the invention.

Figure 8:
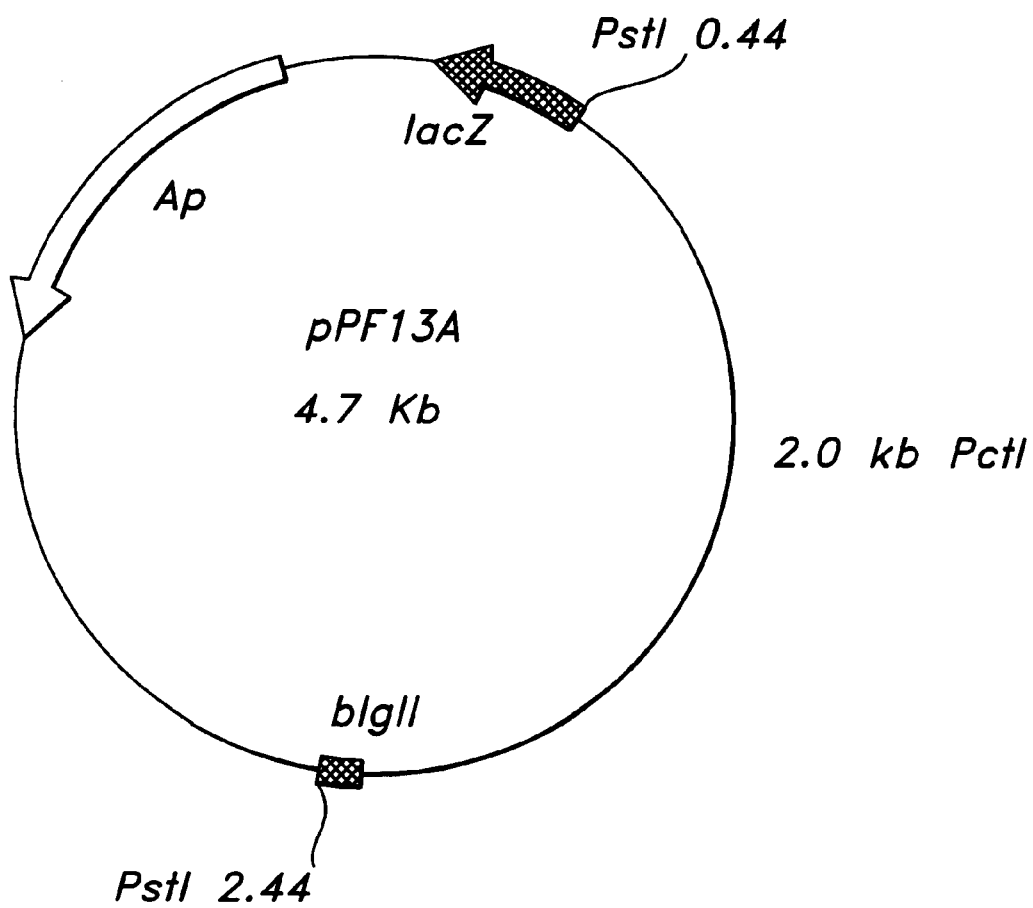

FIG. 8 shows the map of plasmid pPF13A (comprising the 2.0 kb PstI fragment).

DETAILED DESCRIPTION OF THE INVENTION

The present invention is the result of further investigations disclosed in WO 96/12013 (Novo Nordisk A/S) related to a novel enzyme with β-1,3-glucanase activity. Chromosomal DNA from *Oerskovia xanthineolytica* strain LLG109 was analysed by Southern blot hybridization using a PCR-generated probe corresponding to a 180 bp fragment internal to a β-1,3-glucanase gene from the same strain. This resulted in detection of multiple bands of hybridization corresponding to different BamHi and/or KpnI generated DNA fragments (e.g. >10 kb and 2.7 kb BamHI fragments). The co-pending application (i.e. (WO 96/12013) relates to the enzyme exhibiting β-1,3-glucanase activity resulting from the 2.7 kb BamHI fragment. The present invention relates to the enzyme resulting from the >10 kb BamHI fragment.

Said further investigations have led to isolation of another novel β-1,3-glucanase substantially free of protease activity) from *O. xanthineolytica*. When using the novel β-1,3-glucanase of the invention, to get access to a desired intercellular component, the recovery process is facilitated. The novel enzyme opens up the cells in a gently way, which involves making large and porous pores in the cell walls. This will further lead to a reduced amount of contaminants.

Furthermore, said gene encoding the novel β-1,3-glucanase of the present invention can be expressed in a suitable heterologous host cell. A number of strains of *Bacillus subtilis* suitable for large scale industrial production, can be used for production of said enzyme of the present invention.

the DNA sequence of the invention encoding an enzyme exhibiting β-1,3-glucanase activity may be isolated by a general method involving cloning, in suitable vectors, a DNA construct from *Oerskovia xanthineolytica* LLG109, transforming suitable host cells with said vectors, culturing the host cells under suitable conditions to express any enzyme of interest, screening for positive clones by determining any β-1,3-glucanase activity of the enzyme produced by such clones, selection of clones, and isolating the enzyme encoding DNA from such clones.

The general method is further disclosed in WO 93/11249 which is hereby incorporated by reference. A more detailed description of the method is given below.

The DNA sequence coding for the enzyme may for instance be isolated from *Oerskovia xanthineolytica* strain LLG109 (Lechevalier, (1972), Int. J. Sys. Bacteriol. 22 (4), p. 260), and selecting for clones expressing the appropriate enzyme activity (i.e. β-1,3-glucanase activity as defined by the ability of the enzyme to hydrolyse β-1,3-glucan bonds of a suitable substrate such as laminarin or AZCL-curdlan, of the Materials and Methods section hereinafter).

The appropriate DNA sequence may then be isolated from the clone by standard procedure, e.g. as described in the Materials and Methods section.

In the first aspect the invention relates to a DNA construct comprises a DNA sequence, which DNA sequence comprises a) a β-1,3-glucanase activity encoding part of the DNA sequence shown in SEQ ID No. 1 and SEQ ID No. 12, or b) an analogue of the DNA sequence defined in a), which i) is homologous with the DNA sequence defined in a), or ii) hybridizes with the same oligonucleotide probe as the DNA sequence defined in a), or iii) encodes a polypeptide which is homologous with the polypeptide encoded by a DNA sequence comprising the DNA sequence defined in a), or iv) encodes a polypeptide which is immunologically reactive with an antibody raised against the purified β-1,3-glucanase derived from *Oerksovia xanthineolytica* LLG109 encoded by the DNA sequence defined: in a).

The the DNA sequence shown in SEQ ID No. 12 is a corrected version of SEQ ID No. 1. SEQ ID NO. 12 encodes to the best of the inventors' knowledge a novel enzyme with β-1,3-glucanase activity derived from *Oerskovia xanthineolytica* LLG109.

The invention also relates to a DNA construct comprising a DNA sequence encoding a putative mannose binding domain. Said sequence is shown in SEQ ID No. 14, which DNA sequence comprises a1) the part of the DNA sequence shown in SEQ ID No. 14 encoding a mannose binding domain, b) an analogue of the DNA sequence defined in a1), which i) is homologous with the DNA sequence defined in a1), or ii) hybridizes with the same oligonucleotide probe as the DNA sequence defined in a1), or iii) encodes a polypeptide which is homologous with the polypeptide encoded by a DNA sequence comprising the DNA sequence defined in a1), or iv) encodes a polypeptide which is immunologically reactive with an antibody raised against the purified mannose binding donaim derived from *Oerskovia xanthineolytica* LLG109 encoded by the DNA sequence defined in a1).

The β-1,3-glucanase domain and the mannose bind domain are connected via a "hinge" (e.g. a truncation site around amino acids Gly (251) Thr(252) in SEQ ID No 11) which are easily broken. When said two doamins, the β-1,3-glucanase domain and the mannose bind domain, respectively, are hinged together, the enzyme further exhibits a lytic activity.

The full length gene encoding the mature enzyme encoding β-1,3-glucanase activity with a mannose binding domain and pre-pro peptide is shown in SEQ ID No. 10 and SEQ ID NO 11.

The invention also relates to a DNA construct comprising a DNA sequence encoding an enzyme exhibiting β-1,3-glucanase activity having a mannose binding domain, which DNA sequence comprises a2) the part of the DNA sequence shown in SEQ ID No. 10 encoding a β-1,3-glucanase with a mannose binding doamin, b2) an analogue of the DNA sequence defined in a2), which
   i) is homologous with the DNA sequence defined in a2), or
   ii) hybridizes with the same oligonucleotide probe as the DNA sequence defined in a2), or
   iii) encodes a polypeptide which is homologous with the polypeptide encoded by a DNA sequence comprising the DNA sequence defined in a2), or
   iv) encodes a polypeptide which is immunologically reactive with an antibody raised against the purified β-1,3-glucanase with a mannose binding domain derived from *Oerskovia xanthineolytica* LLG109 encoded by the DNA sequence defined in a2).

The DNA sequence shown in SEQ ID No. 12 and SEQ ID No. 14, encoding an enzyme with β-1,3-glucanase and the mannose binding domain, respectively, constitutes the full length DNA sequence shown in SEQ ID No. 10.

The ORF encodes a precursor of 435 amino acids, $M_W$ 46,102 Da with a pre-pro peptide of 52 amino acids (SEQ ID NO. 11). The mature β-1,3-glucanase (including the mannose binding doamin) is a 383 amino acid polypeptide with a molecular weight of 40,814 Da and a predicted pI of 5.93.

The molecular weight of said native β-1,3-glucanase found in the *Oerskovia xanthineolytica* LLG109 supernatant was determined experimentally by matrix assisted laser desorption ionisation time-of-flight mass spectrometry in a VG Analytical TofSpec to be 27,196 da. The theoretical molecular weight of the amino acid sequence shown in SEQ ID No 11 was calculated to 28,120 da, indicating a post-secretional proteolytical processing of the C-terminal end of the molecule, cleaving about 10 amino acids, probably 13 amino acids to give the predicted site of 251 amino acids, molecular weight of 27,191 and pI of 5.46.

The pI determined by Ventom and Asenjo, (1991), supra, was 5.0, slightly deviating from the calculated value and indicating that some charged groups are buried in the structure.

This proves that the enzyme of the present invention is not the same enzyme as the enzyme cloned in the co-pending application WO 96/12013 (from Novo Nordisk A/S)

A preferred method for amplifying specific DNA sequences is the polymerase chain reaction (PCR) using degenerate oligonucleotide probes. PCR may for instance be carried out using the techniques described in U.S. Pat. No. 4,683,202 or by R. K. Saiki et al. (1988).

It is expected that a DNA sequence coding for homologous proteins, i.e. an analogous DNA sequence, is obtainable from other microorganisms. For instance, the DNA sequence may be derived from another microorganism, in particular either a fungus or a bacterium.

Such DNA sequences may originates from fungi, comprising a strain of an Asperguillus sp., in particular a strain of *A. aculeatus* or *A. niger*, a strain of Trichoderma sp., in particular a strain of *T. reesie, T. viride, T. longibrachiatum* or *T. koningii, T. harzianum* or a strain of a Fusarium sp., in particular a strain of *F. oxysporum*, or a strain of a Humicola sp.

Further, a DNA sequence encoding a homologous protein may be expected to derive from bacteria, such as another strain of a Oerskovia sp., or a strain of an Arthrobacter sp., Cytophaga sp., Rhodothermus sp., in particular a strain of *Rh. marinus*, or a strain of a *Clostrium*, in particular strains of *Cl. thermocellum*, or a strain of a *Bacillus*, in particular strains of *B. licheniformis., B. amyloliquefaciens*, or *B. circulans*.

Alternatively, the DNA coding the enzyme/protein of the invention may, in accordance with well-known procedures, conveniently be isolated from DNA from any of the above mentioned organisms by use of synthetic oligonucleotide probes prepared on the basis of the DNA sequence shown in SEQ ID No. 1, 10, 12 and 14, or a part thereof.

The DNA sequence in question may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector; i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the enzyme/protein of the invention should be operably connected to a suitable promoter and terminator sequence. The promoter may be any DNA sequence which shows transcriptional activity in the host cell of choice and may be derived from genes encoding proteins either homologous or heterologous to the host cell.

It is preferred to use a vector under control of the promoter for the maltogenic β-1,3-amylase from *Bacillus stearothermophilus* and/or the signal of *Bacillus stearothermophilus*.

In a specific embodiment the expression vector comprise plasmid pLHed1 (see FIG. 5) encoding an enzyme with β-1,3-glucanase activity and pLHed2 (see FIG. 7) encoding an enzyme with β-1,3-glucanase activity having a mannose binding domain.

An expression vector for producing the mannose binding domain (i.e. SEQ ID NO. 15) of the invention can be constructed the same way as described in Example 3 and 4.

The procedures used to ligate the DNA sequences coding for the enzyme/protein, the promoter, and the terminator, respectively, and to insert them into suitable vectors are well known to persons skilled in the art (cf., for instance, Sambrook et al., (1989), Molecular Cloning. A Laboratory Manual, Cold Spring Harbor, N.Y.).

Host cells, which can be transformed with the DNA sequence encoding the enzyme/protein of the invention, may be either eukaryotic or prokaryotic.

Suitable prokaryotic host cells are bacterial cells.

Examples of such bacterial host cells which, on cultivation, are capable of producing the novel enzyme of the invention are grampositive bacteria such as strains of *Bacillus* such as strains of *B. subtilis, B. licheniformis, B. lentus, B. brevis, B. stearothermophilus, B. alkalophilus, B.*

*amyloliquefaciens, B. coagulans, B. circulans, B. lautus, B. megaterium* or *B. thuringiensis*, or strains of *Streptomyces*, such as *S. lividans* or *S. murinus*, or gramnegative bacteria such as *Escherichia coli*. The transformation of the bacteria may be effected by protoplat transformation or by using competent cells in a manner known per se (cf. Sambrook et al., (1989), supra).

In specific embodiments of the invention the bacterial host cell a *Bacillus subtilis*, especially the strain *B. subtilis* DN1885, or a protease deficient strain of *Bacillus*, such as *B. subtilis* ToC46.

When expressing the enzyme/protein in bacteria such as *E. coli*, the polypeptide may be retained in the ctyoplasm, typically as insoluble granules (known as inclusion bodies), or may be directed to the periplasmic space by a bacterial secretion sequence. In the former case, the cells are lysed and the granules are recovered and denatured after which the polypeptide is refolded by diluting the denaturing agent. In the latter case, the polypeptide may be recovered from the periplasmic space by disrupting the cells, e.g. by sonication or osmotic shock, to release the contents of the periplasmic space and recovering the polypeptide.

Suitable eukaryotic cells are, in particular fungal cells, such as a yeast or filamentous fungal cells.

Examples of suitable yeasts cells include cells of Saccharomyces spp., in particular strains of Saccharomyces cervisiae, Saccharomyces kluyveri, Sacchromyces uvarum, or Schizosaccharomyces spp., such as Schizosaccharomyces pombe. Methods for transforming yeast cells with heterologous DNA and producing heterologous polypeptides there from are described, e.g. in U.S. Pat. No. 4,599,311, U.S. Pat. No. 4,931,373, U.S. Pat. Nos. 4,870,008, 5,037,743, and U.S. Pat. No. 4,845,075, all of which are hereby incorporated by reference. Transformed cells are selected by a phenotype determined by a selectable marker, commonly drug resistance or the ability to grow in the absence of a particular nutrient, e.g., leucine. A preferred vector for use in yeast is the POT1 vector disclosed is U.S. Pat. No. 4,931, 373. The DNA sequence encoding the polypeptide of the invention may be preceded by a signal sequence and optionally a leader sequence, e.g. as described above. Further examples of suitable yeast cells are strains of Kluyveromyces spp., such as *K. lactis*, or Hansenula spp., e.g.

H. polymorpha, or Pichia spp., e.g. *P. pastoris*, Yarrowia spp., such as *Yarrowia lipolytica* (cf. Gleeson et al., (1986), J. Gen. Microbiol. 132, p. 3459–3465; U.S. Pat. No. 4,882, 279).

Examples of other fungal cells are cells of filamentous fungi, e.g. Aspergillus spp., Neurospora spp., Fusarium spp. or Trichoderma spp., in particular strains of *A. oryzae, A. niculans* or *A. niger*. The use of Aspergillus spp. for the expression of proteins is described in, e.g., EP 272 277, EP 238 023 and EP 184 438. The transformation of *F. oxysporum* may, for instance, be carried out as described by Malardier et al., (1989), Gene 78, p. 147–156.

When a filamentous fungus is used as the host cell, it may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

In a yet another aspect, the present invention relates to a method of producing the enzyme/protein of the invention, wherein a suitable host cell transformed with a DNA sequence encoding the enzyme/protein is cultured under conditions permitting the production of the enzyme/protein, and the resulting enzyme/protein is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type culture Collection).

The expressed enzyme/protein produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, eg. ion exchange chromatography, gel filtration chromatography, affinity chromatography, or the like, dependent on the type of polypeptide in question.

In a still further aspect, the present invention relates to an novel enzyme preparation useful for the modification or degradation of β-glucan containing materials, said preparation being enriched in an enzyme exhibiting β-1,3-glucanase activity as described above.

The enzyme preparation having been enriched with the novel β-1,3-glucanase enzyme of the invention may e.g. be an enzyme preparation comprising multiple enzymatic activities, in particular an enzyme preparation comprising different enzyme activities required for the modification or degradation of microbial cell walls.

Examples of such enzyme preparations include lytic enzyme systems, in particular of microbial (fungal or bacterial) origin, e.g. derived from a strain of Trichoderma, such as *Trichoderma harzianum, Trichoderma viride* or *Trichoderma reesie*, a strain of Oerskovia sp., such as *Oerskovia xanthineolytica*, a strain of Arthrobacter sp. such as *Arthrobacter luteus*, a strain of Rhizoctonia sp. or Cytophaga sp., a strain of a Staphylococcus sp., or a strain of Streptomyces sp..

Specifically contemplated in this connection is an enzyme preparation enriched with the β-1,3-glucanase with a mannose binding domain of the invention.

Commercially available enzyme preparations which may conveniently be boosted with an enzyme of the invention include Novozyme® 234 and Cerefle® 200L, both available from Novo Nordisk A/S, Denmark, Cellolase (available from Merck), Cellulase CP and Cellulase CT (both available from Sturge), and/or Chitinase (available from Sigma), Zymolase from Kirin Breweries.

In the present context, the term "enriched" is intended to indicate that the β-1,3-glucanase with/without a mannose binding domain has been increased, e.g. with an enrichment factor of at least 1.1, conveniently due to addition of an enzyme of the invention prepared by the method described above.

Alternatively, the enzyme preparation enriched in an enzyme exhibiting β-1,3,- glucanase with/without a mannose binding domain may be one which comprise enzyme(s) of the invention as the major enzymatic component, e.g. a mono-component enzyme composition.

The enzyme preparation may be prepared in accordance with methods known in the art and may be in the form of a liquid or a dry preparation. For instance, the enzyme preparation may be in the form of a granulate or a microgranulate. The enzyme to be included in the preparation may be stabilized in accordance with methods known in the art.

The enzyme preparation of the invention may, in addition to an enzyme of the invention, contain one or more other cell wall degrading enzymes, for instance those with cellulytic, mannanolytic, chitinolytic or proteolytic activities such as endo- and exo-glucanase, mannanase, endo- and exo-chitinase, protease, or α- or β-mannosidase. The additional enzyme(s) may be producible by means of a microorganism belonging to the genus Aspergillus, preferably *Aspergillus niger, Aspergillus aculeatus, Aspergillus awamori* or *Aspergillus oryzae*, or the genus Trichoderma, or the genus Oerskovia, the genus Cytophaga, or the genus Arthrobacter or any of the microorganisms mentioned above in connection with the commercially available enzyme preparations.

Examples are given below of preferred uses of the enzyme preparation of the invention. The dosage of the enzyme composition of the invention and other conditions under which the composition is used may be determined on the basis of methods known in the art.

The enzyme preparation according to the invention is preferably used as an agent for degradation or modification of β-glucan containing material such as microbial cell walls. In particular, the enzyme preparation of the invention may be used for rupturing or lysing cell walls of microorganisms thereby enabling recovery of desirable products produced by the microorganism.

It will be understood that the specific composition of the enzyme preparation to be used should be adapted to the composition of the cell wall to be ruptured or lysed. For instance, yeast cell walls have been found to comprise two main layers, an outer layer of protein-mannan complex and an inner glucan layer. In order to efficiently rupturing the cell wall of yeast it is desirable that the enzyme preparation comprises at least protease, mannanase and β-glucanase activity.

The extract recovered after rupture of the microbial cell walls normally comprises a number of different components, such as pigments, vitamins, colorants and flavourants. Extracts obtained from rupture of yeast, i.e. yeast extracts, are used as such, e.g. for food or feed applications—or components thereof may be recovered and optionally further processed.

Examples of such products include vitamins, colorants (e.g. carotenoids, Q-10 and astaxanthin), enzymes, proteins and flavour components or flavour enhancers (e.g. MSG, 5'-GMP and 5'-IMP). The products to be recovered may be inherent products of the microorganism in question, or may be products which the microorganism has been constructed to produce, e.g. recombinant products.

In addition, the enzyme preparation of the invention may be used in the production of protoplasts from yeasts (e.g. of Saccharomyces sp. or Schizosaccharomyces sp.) or from fungi (e.g. Aspergillus sp. or Penicillium sp.). Preparation and regeneration of protoplast from such organisms are important in fusion, transformation and cloning studies. The production of protoplasts may be performed in accordance with methods known in the art.

The invention may also be used for improving fungal transformation.

Further the enzyme or enzyme preparation according to the invention may be used in the preparation of pharmaceuticals, especially products entrapped inside the cells, in the cytoplasmic membrane, the periplasmic space and the cell wall.

In addition, the enzyme preparation of the invention may be used in the modification of β-glucans such as curdlan and laminarin.

The invention is described in further detail in the following examples which are not in any way intended to limit the scope of the invention as claimed.

METHODS AND MATERIALS

Donor Organism:
  *Oerskovia xanthineolytica* LLG109 (M. Lechevalier, (1972), Int. J. Sys. Bacteriol. 22(4), p. 260)
Deposited Microorganisms:
  *Oerskovia xanthineolytica* LLG109 strain has been deposited at the Duetsche Sammlung von Mikroorganismen und Zellkulturen GmbH., (DMS).
  Deposit date: 13.10.95
  Depositor's ref.: NN049107 (*Oerskovia xanthineolytica* LLG109)
  DSM designation: *Oerskovia xanthineolytica* (or *Cellulomonas cellulans*) DSM Nop. 10297.
Host Organism:
  *E. coli* Max Efficiency DHα™ competent cells (Gibco-BRL) (cells prepared according to BRL modificated procedure of Hannan, O. (1983), J. Mol. Biol. 166, p. 557.
  *E. coli* JM109 (Yanish-Perron et al., (1985), Gene 33, p. 103–199)
  *B. subtilis* DN1885 (Diderichsen et al., (1990), Journal of Bacteriology, vol. 172, p. 4315–4321)
  *Bacillus subtilis* protease deficient strain ToC46 (Diderichen et al., (1990), Journal of Bacteriology, vol. 172, p. 4315–4321.
Primers:
  140D: 5' gtggatgggcagcagtcc 3' (see SEQ ID NO 3)
  143U: 5' gtagacgcggacgtaatc 3' (see SEQ ID NO 4)
  Primers for amplification of the 180 bp fragment.
  DK1:
  5' gcaatcgattgcattacgaaag 3' (see SEQ ID NO 5)
  DK2:
  5' gaggtcgccgggcgcggcttcagcggcgtttggattg 3' (see SEQ ID NO 6)
  DK3:
  5' aacgccgctgaagccgcgcccggcgacctcctgtgg 3' (See SEQ ID NO 7)
  DK4:
  5' gtcggatcctgcagctgcacgtgacgatctgcacc 3' (See SEQ ID NO 8)
  DK5:
  5' AACACGATCGGTCGACCCGCCCGACGACGC 3' (see SEQ ID no. 9)

Figure 1:
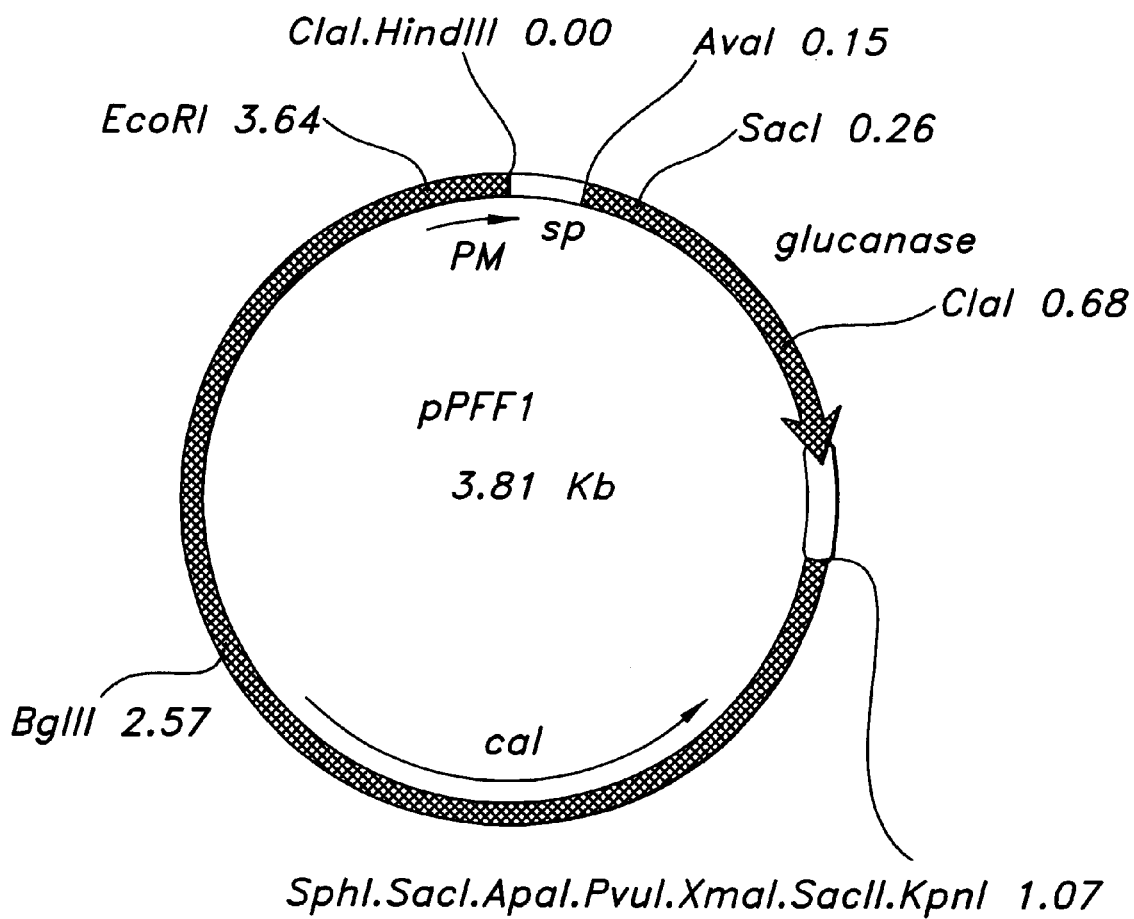
FIG. 1 shows the physical map of plasmid pPFF1, PM: Promoter from the maltogenic α-amylase from B.

| Plasmids: | |
|---|---|
| pPFF1: | See FIG. 1 |
| pPF10: | 7.1 kb BamHI-KpnI fragment and 2.25 kb PstI fragment from *O. xanthineolytica* LLG109 (See FIG. 3). |
| pPF12A | 2.25 kb PstI fragment of pPF10 in pUC18 (See Fig. 4) |
| pPF13A | 2.0 PstI fragment of pPF10 in pUC18 comprising a 50 bp fragment of the glucanase gene lacking in the 2.25 kb PstI fragment in pPF12A (see FIG. 8). |
| pLHed1 | 3.7 kb plasmid comprising the 1.0 kb ClaI-PstI fragment in plasmid pDN2801 (see SEQ ID NO. 1 (corrected to SEQ ID No. 12)) |
| pLHed2 | 4.1 kb plasmid comprising the 1.4 kb ClaI-PvuI fragment in plasmid pDN2801 (see SEQ ID NO. 10 and FIG. 7) |
| pUC18: | from Gibco-BRL |
| pDN2801 | (Diderichsen et al., (1990), Journal of Bacteriology vol. 172, p. 4315–4321). |
| pDN520 | (Diderichsen et al., (1988), FEMS, Microbiol. Lett. 56, p. 53–60). |

Promoter:
  Maltogenic α-amylase from *Bacillus stearotherophilus* (Diderichen et al., (1988), FEMS, Microbiol. Lett. 56, p. 53–60)

Kits:
  Prime-a-Gene® DNA labelling Kit (Promega)
  Wizard Clean-up DNA purification kit (Promega)
  Taq DNA Polymerase (Promega)
  SEQUENASE™ sequencing kit (USBI)
Equipment:
  charged modified nylon membrane, 0.45 μm pore size (Sigma) nylon membrane (Hybond-N, Amersham)
  VG Analytical TofSpec (VG Analytical, Manchester, UK)
METHODS:
  Isolation of genomic DNA: chromosomal DNA from *O. xanthineolytica* is prepared according to Meade et al., J. Bacteriol. 149(1), p. 114–122, 1982)
Gel Electrophoresis of DNA and Southern Blotting
  Agarose gel electrophoresis, and Southern Blotting, is used to analyze plasmids, restriction endonuclease fragments, ligation products, PCR reaction, according to Sambrook et al., (1989), supra.
  Recovery of DNA from agarose gels is done according to Sambrook et al., (1989), supra.
Radiolabelling of Double-Stranded DNA Fragments
  Purified DNA fragments is $^{32}$P-labelled with [α32P]-dATP (3000 Ci/mmol. Dupont) using oligonucleotide priming kit (Prime-a-Gene® DNA labelling Kit) following the manufacturer's instructions.
Southern Blot Hybridization Analysis Conditions
  Hybridization of Southern blots on nylon filters (Hybond-N, Amersham) with $^{32}$P-labelled PCR probe is carried out following methods described by Sambrook et al., (1989), supra. The membrane is placed in a plastic bag and pre-hybridized in 50% (v/v) formamide, 6xSSC, 0.05x BLOTTO, 1 mM EDTA at 42° C. for 1–2 hours. Then the membrane is hybridized with the radiolabelled and denaturated DNA probe in 50% (v/v) formamide, 6xSSC, 0.5% (w/v) SDS, 1 mM EDTA at 42° C. (which corresponds to a temperature of 68° C. without formamide in the hybridization solution, overnight. After hybridization, the membrane is washed first in 2xSSC, 0.5% (w/v) SDS and then with 0.1xSSC, 0.5% (w/v) SDS at 50° C. Then, the membrane is wrapped in Saran Wrap and exposed to X-ray Film at −70° for the requested period of time.
PCR (Polymerase Chain Reaction) Amplification:
  PCR Amplification from *O. xanthineolytica* LLG109
  The PCR Reactions are carried out using 100 pmols of each degenerate primer per reaction. An amount of 100 ng of Oerskovia DNA is used per reaction. Taq DNA Polymerase is used. The conditions recommended by the manufacturer. Cycling conditions were as followed: Hot start: 95° C. for 1 minute, 40 cycles.
  The PCR product is cloned into pUC18/SmaI as described by Kanungo and Pandey, (1993), Biotechniques 14(6), p. 912, for subsequent sequencing.
Dideoxynucleotide-Chain-Termination Method:
  The method is carried out as described by Sanger et al., (1977), Proc. Natl. Acad. Sci. U.S.A. 74, p. 5463–5467, using the Sequenase® version 2.0 kit (USB-Amersham), [α-35S]dATP (specific activity of 1000 Ci/mmol, Dupont) following the manufactures instructions. All reactions are performed directly on double-stranded plasmid DNA templates. Plasmid DNA is alkaline denaturated as described in the Sequenase® kit protocol book. Occasionally, template DNA is denaturated by heat denaturation as described by Andersen et al., (1992), BioTechniques 13, p. 678–679.
Transformation of *E. coli*:
  *E. coli* Max Efficiency DHα™ competent cells is transformed by heat shock as indication by the manufacture.
transformation of *B. subtilis*:
  Competent cells are prepared and transformed as described by Yasbin, R. E., Wilson, G. A. and Young, F. E., (1975), J. Bacteriol. vol. 121, p. 296–304.
Identification of Positive Clones:
  The identification is done according to Sambrook et al., (1989), supra.
DNA Sequencing
  DNA sequencing is done using SEQUENASE™ sequencing kit following the manufactures recommendations. DNA compressions are resolved by using the reagent kit for DNA sequencing using 7-deaza-dGTP and Sequenase® (from USBI).
Isolation of Plasmid DNA:
  *E. coli*: The isolation of *E. coli* plasmid is done according to Sambrook et al., (1989), supra, using the method described in Promega Protocols and Application Guide).
  *B. subtilis*: the isolation of *B. subtilis* is done according to Kieser, T, (1984), Plasmid 12, p. 19–36.
Mass Spectrometry
  Matrix assisted laser desorption ionisation time-of-flight mass spectrometry of the purified recombinant β-1,3-glucanase is carried out in a VG Analytical TofSpec. For mass spectrometry 2 μl of sample is mixed with 2 μl saturated matrix solution (α-cyano-4-hydroxycinnamic acid in 0.1% TFA: acetonitrile (70:30) and 2 μl of the mixture onto the target plate. Before introduction into the mass spectrometer the solvent is removed by evaporation. Samples are desorbed and ionised by 4 ns laser pulses (337 nm) at threshold laser power and accelerated into the field-free flight tube by an accelerating voltage of 25 kV. Ions are detected by a micro channel plate set at 1850 V. The spectra are calibrated externally with proteins of knows mass.
  Immunological cross-reactivity: Antibodies to be used in determining immunological cross-reactivity may be prepared by use of a purified β-1,3,-glucanase. More specifically, antiserum against the β-1,3-glucanase of the invention may be raised by immunizing rabbits (or other rodents) according to the procedure described by N Axelsen et al. in: A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically p. 27–31). Purified immunoglobulins may be obtained from the antisera, for example by salt precipitation (($NH_4)_2$ $SO_4$), followed by dialysis and ion exchange chromatography, e.g. on DEAE-Sephadex. Immunochemical characterization of proteins may be done either by Outcherlony double-diffusion analysis (O. Ouchterlony in: Handbook of Experimental Immunology, (D. M. Weir, Ed.), Blackwell Scientific Publications, (1967), p. 655–706), by cross immunoelectrophoresis (N. Alelsen et al., supra, Chapters 3 and 4), or by rocket immunoelectrophoresis (N. Axelsen et al., Chapter 2).

| Media |  |
|---|---|
| LB agar | |
| Bacto-tryptone | 10 g/l |
| Bacto yeast extract | 5 g/l |
| NaCl | 10 g/l |
| Bacto agar | 15 g/l |
| adjusted to pH 7.5 with NaOH | |

All autoclaved at 121° C., 30 minutes.
Enzymes:
  Native β-1,3-glucanase from *Oerskovia xanthineolytica* LLG109 (Ventom and Asenjo, (1991), Enzyme Microb. Technol. 13, p. 71)

Substrate:
  AZCL-curdlan: Megazyme, Sydney, Australia
  Laminarin: Sigma
Enzyme Assay:
  Assay Conditions:
    Shaking waterbath, 37° C., 1 hour.
    Incubation mixture: 0.5 mls supernatant+0.5 mls 1 w/v% AZCL-curdlan+0.5 mls acetatebuffer (pH 4.0). Curdlan was also dissolved in the acetatebuffer. Reaction stopped with 3 mls of stop reagent. The insoluble curdlan spun down by centrifugation and the dissolved blue coloured part determined on a Hitachi Spectrophotometer at 590 nm, 1 cm.

| Stop reagent: | |
|---|---|
| Sodiumacetate | 40 grams |
| Zinkacetate | 4 grams |
| Deionized water to | 200 mls | pH is adjusted to 5.0 before mixing with 800 mls of 2-methoxy-ethanol.

EXAMPLES

Example 1

Construction of a Genomic DNA Partial Library for O. xanthineolytica LLG109

Genomic DNA from O. xanthineolytica LLG109 was prepared as described above and amplfied by PCR. 10 μg was digested with BamHI and KpnI. The digested DNA was fractionated by electro-phoresis on a 1.0% (w/v) low melting point agarose gel, 1×TAE buffer. Fragments ranging from 6 to 10 kb were cut out from the gel. Agarose slices (in 300 mg pieces) were melted at 65° C. for 5 minutes and subsequently purified with Wizard clean-up DNA purification kit.

Also plasmid pUC18 was equally digested with BamHI and KpnI. Linearized plasmid was separated by electro-phoresis as described above and purified with the restriction fragments from genomic DNA.

50 ng pUC18 and 150 ng genomic DNA fragments were ligated with T4 DNA ligase at 16° C., overnight, in a 20 μl reaction. After incubation, the ligation solution was diluted 1:5 with TE buffer pH 7.5. E. coli Max Efficiency DHα™ competent cells were transformed by heat shock at 42° C. with 5 μl of the diluted ligation solution. Transformants were grown on LB agar plates containing X-Gal and IPTG (Sambrook et al., (1989), supra), and 100 g/ml Ampicillin.

About 1000 transformants were obtained, and 700 of these were individually picked with sterile toothpicks and replication in two additional plates, Master and Copy, respectively. Copy plates were used to replica plate the colonies onto nylon membranes as described by Sambrook et al, (1989), supra). Colony blots were hybridized to the 180 bp insert from pPFPCR6 using the conditions described above.

A positive clone, pPF10, comprising an 7.1 BamHI-KpnI insert was isolated. A PCR product of 180 bp could be amplified from the DNA plasmid construct using the primers 140D (SEQ ID NO 3) and 143U (SEQ ID NO 4) designed according to the 180 bp probe sequence (see FIG. 2). Also a Southern Blot analysis of pPF10 using the same 180 bp probe revealed that a 2.25 kb PstI fragment was comprised in the insert hybridized to the probe.

This 2.25 kb PstI fragment was subcloned into the PstI site of pUC18 using analogous procedures as those described above. The resulting construct, pPF12A (see FIG. 4) was partially analysed by restriction mapping with SmaI and showed to contain a 0.7 kb fragment and a number of smaller fragments, one of them about 0.3 kb.

Example 2

Nucleotide Sequence of the β-1,3-glucanase Gene

Plasmid pPF10 was used for sequencing purposes. Southern blot analysis of pPF10 using the 180 bp PCR probe indicated that the ORF of the glucanase gene (or part thereof) was present on the 2.25 kb PstI fragment of pPF10. However, partial nucleotide sequencing of pPF12A (comprising the 2.25 kb PstI fragment) revealed that it did not contain the entire ORF for the glucanase gene. Therefore, the 2.0 kb PstI fragment present in the pPF10 insert, and contiguous to the 2.25 kb PstI fragment was also subcloned into pUC18 (i.e. pPF13A) following the procedure used for constructing pPF12A.

The nucleotide sequences of the 2.25 kb PstI fragment of pPF12A and the 2.0 kb PstI fragment of pPF13A (together comprising the DNA sequence(s) of the invention(i.e. SEQ ID NO 1, 10, 12 and 14) were determined by the dideoxynucleotide-chain-termination method. Double-stranded DNA was denaturated by alkali or heat treatment before using it as a template for sequencing reactions. Both strands of this region from pPF12A and pPF13A were sequenced according to the sequence strategy shown.

The complete nucleotide sequences encoding active enzyme and the deduced mature amino acid sequences are shown in SEQ ID NO 1 (corrected to SEQ ID No. 12) and SEQ ID NO 2 (corrected to SEQ ID NO. 13), respectively, and the full length sequence SEQ ID NO. 10 and SEQ ID No 11, respectively.

Example 3

Cloning and Expression of the β-1,3-Glucanase Gene (SEQ ID No. 12) in Bacillus subtilis Expression of the β-1,3-glucanase gene is performed by replacing the native expression signals with those from the well-expressed Bacillus stearothermophilus maltogenic α-amylase. A 1.0 kb ClaI-PstI fragment made by SOE-PCR is cloned on plasmid pDN2801 (Diderichsen et al. (1990), supra) in the ClaI-PstI opening.

A perfect fusion of the nucleotide sequence for the promoter, RBS and signal peptide maltogenic α-=amylase gene from Bacillus stearothermophilus and the N-terminal of the β-1,3-glucanase gene ORF, including the terminator is made. This final construct pLHed1 is made as follows. The PCR fragment is obtained by SOE-PCR (Horton et al., (1989), Gene, 77, p. 61–68). Two separate PCR reactions are performed using pDN520 or ppPF12A respectively as templates. In the first PCR reaction primer DK1 and DK2 are used. In the second PCR reaction primer DK3 and DK4 are used.

Both PCR reactions are performed by standard procedures using temperatures of 96° C. at denaturation, 55° C. at annealing and 72° C. at the extension step. A total of 20 cycles were performed. formed. Both fragments are purified from an agarose gel and 500 ng of each are used for a second 5 cycle PCR reaction: 96° C. for 2 minutes, 50° C. for 5 minutes and 72° C. for 1 minute.

Primer KB1 and DK4 (100 pmol) are added at 96° C. and a third 25 cycle PCR reaction is initiated: 96° C. for 30 seconds, 55° C. for 30 seconds and 72° C. for 90 seconds. The final PCR fragment is digested with ClaI-PstI and ligated to pDN2801 digested with ClaI-PstI and the ligation mixture containing pLHed1 is transformed into *Bacillus subtilis* DN1885 (Yasbin et al, 1975). In this case β-1,3-glucanase activity is detected after 24 hours growth at 37° C. on LB plates containing 0.04% laminarin by staining with congo red.

In the same way pLHed1 is finally also transformed into the protease deficient host *Bacillus subtilis* ToC46.

Example 4

Cloning and Expression of the β-1,3-glucanase with a Mannose binding domain (SEQ ID NO. 10) in *Bacillus subtilis*

Expression of the β-1,3-glucanase gene with the mannose binding domain was performed by replacing the native expression signals with those from the well-expressed *Bacillus stearothermophilus* maltogenic α-amylase. A 1.4 kb ClaI-PvuI fragment made by SOE-PCr was cloned on plasmid pDN2801 (Diderichsen et al. (1990), supra) in the ClaI-PvuI opening.

A perfect fusion of the nucleotide sequence for the promoter, RBS and signal peptide maltogenic α-amylase gene from *Bacillus stearothermophilus* and the N-terminal of the β-1,3-glucanase gene ORF, including the terminator was made. This final construct pLHed2 (see FIG. 7) was made as follows.

The PCR fragment was obtained by SOE-PCR (Horton et al., (1989), Gene 77, p. 61–68). Two separate PCR reactions were performed using pPF10 as templates.

The pPF10 template was predenaturated before PCR amplification by alkaline denaturation with 0.1 volume of 0.2 M NaOH, 10 mM EDTA for 30 minutes at 37° C., neutralised with 0.1 volumes of 3M Na Acetate, pH 5.2, and precipitated with 2.5 volume ethanol.

In the first PCR reaction primer DK1 and DK2 were used. In the second PCR reaction primer DK3 and DK5 were used.

Dimethyl Sulfoxide (DMSO) was added to a final concentration of 10% in the PCR reaction to facilitate initiation of amplification by DK3 and DK5 as described by Filichkin et al. (1992), Biotechniques 12(6), p. 828–830.

Both PCR reactions were performed using temperatures of 96° C. at denaturation, and 55° C. (for DK1/DK2) and 65° C. (for DK3/DK5) at annealing and 72° C. at the extension step. A total of 20 cycles were performed. Both fragments were purified from an agarose gel and 500 ng of each were used for a second 5 cycle PCR reaction: 96° C. for 2 minutes, 50° C. for 5 minutes and 72° C. for 1 minute.

Primers DK1 and DK5 (100 pmol) were added at 96° C., and a third 25 cycle PCR reaction was initiated: 96° C. for 30 seconds, 55° C. for 30 seconds and 72° C. for 90 seconds. The final PCR fragment was digested with ClaI-PvuI and ligated to pDN2801 digested with ClaI-PvuI and the ligation mixture containing pLHed2 was transformed into *Bacillus subtilis* DN1885 (Yasbin et al, 1975). In this case β-1,3-glucanase activity was detected after 24 hours growth at 37=20 C. on LB plates containing 0.04% laminarin by staining with congo red.

In the same way pLHed2 was finally also transformed into the protease deficient host *Bacillus subtilis* ToC46.

| ABBREVIATIONS | | |
|---|---|---|
| AMINO ACIDS | | |
| A = | Ala = | Alanine |
| V = | Val = | Valine |
| L = | Leu = | Leucine |
| I = | Ile = | Isoleucine |
| P = | Pro = | Proline |
| F = | Phe = | Phenylalanine |
| W = | Trp = | Tryptophan |
| M = | Met = | Methionine |
| G = | Gly = | Glycine |
| S = | Ser = | Serine |
| T = | Thr = | Threonine |
| C = | Cys = | Cysteine |
| Y = | Tyr = | Tyrosine |
| N = | Asn = | Asparagine |
| Q = | Gln = | Giutamine |
| D = | Asp = | Aspartic Acid |
| E = | Glu = | Glutamic Acid |
| K = | Lys = | Lysine |
| R = | Arg = | Arginine |
| H = | His = | Histidine |
| NUCLEIC ACID BASES | | |
| A = | Adenine | |
| G = | Guanine | |
| C = | Cytosine | |
| T = | Thymine (only in DNA) | |
| U = | Uracil (only in RNA) | |

What is claimed is:

1. An isolated enzyme exhibiting beta-1,3-glucanase activity and having a mannose binding domain, wherein the enzyme is selected from the group consisting of:
   (a) the enzyme encoded by the mature protein-encoding portion of the DNA sequence of SEQ ID NO:10;
   (b) a polypeptide encoded by a DNA sequence which hybridizes to SEQ ID NO:10 under the following conditions: pre-hybridized in 50% formamide, 6×SSC, 0.05×BLOTTO, 1 mM EDTA at 42° C. for 1–2 hours, followed by hybridization with the radiolabelled and denatured DNA probe in 50% formamide, 6×SSC, 0.5% (w/v) SDS, 1 mM EDTA at 42° C., overnight, followed by one wash in 2×SSC, 0.5% SDS, and a second wash with 1×SSC, 0.5% SDS at 50° C.;
   (c) a polypeptide having the amino acid sequence of SEQ ID NO:11, and
   (d) a polypeptide which is 90% homologous with the polypeptide encoded by the DNA sequence of (a).

2. The enzyme of claim 1, having an apparent molecular weight of about 41 kDa.

3. An enzyme preparation useful for modification or degradation of β-glucan containing material, comprising the enzyme of claim 1.

4. The enzyme preparation of claim 3, further comprising at least one second cell wall degrading enzyme selected from the group consisting of enzymes having cellulytic, mannanolytic, chitinolytic or proteolytic activities.

5. The enzyme preparation of claim 4, wherein said second enzyme is selected from the group consisting of endo-glucanases, mannanases, endo- or exo-chitinases, proteases, and α- or β-mannosidases.

6. The enzyme preparation of claim 4, wherein said second enzyme is selected from the group consisting of NOVOZYME® 234 (*Trichoderma harzianum* protease, glucanase and chitinase), CEREFLO® 200L (*Bacillus subtilis* beta-glucanase), cellulase, Cellulase CP, Cellulase CT, and chitinase.

7. A method for the modification or degradation of a β-glucan containing material, said method comprising contacting said material with an enzyme according to claim 1 under conditions suitable for degradation of said material.

8. The method according to claim 7, wherein said material comprises a bacterial cell wall and said method results in formation of protoplast.

9. The method of claim 7, wherein said method results in release of pigments, colorants, flavorants, or yeast extracts.

\* \* \* \* \*